(12) United States Patent
Larter et al.

(10) Patent No.: US 9,528,874 B2
(45) Date of Patent: Dec. 27, 2016

(54) RESERVOIR SAMPLING TOOLS AND METHODS

(75) Inventors: Stephen Richard Larter, Calgary (CA); Barry Bennett, Calgary (CA); Lloyd Ross Snowdon, Calgary (CA)

(73) Assignee: GUSHOR, INC., Calgary (CA)

( * ) Notice: Subject to any disclaimer, the term of this patent is extended or adjusted under 35 U.S.C. 154(b) by 321 days.

(21) Appl. No.: 14/232,899

(22) PCT Filed: Aug. 15, 2012

(86) PCT No.: PCT/CA2012/050554
§ 371 (c)(1),
(2), (4) Date: Mar. 6, 2014

(87) PCT Pub. No.: WO2013/023299
PCT Pub. Date: Feb. 21, 2013

(65) Prior Publication Data
US 2014/0208826 A1 Jul. 31, 2014

Related U.S. Application Data

(60) Provisional application No. 61/524,162, filed on Aug. 16, 2011.

(51) Int. Cl.
*G01N 1/22* (2006.01)
*G01J 1/02* (2006.01)
(Continued)

(52) U.S. Cl.
CPC .................. *G01J 1/02* (2013.01); *E21B 49/06* (2013.01); *E21B 49/10* (2013.01); *G01J 3/42* (2013.01); *G01J 3/44* (2013.01); *G01J 3/443* (2013.01); *G01J 3/4406* (2013.01); *G01N 11/00* (2013.01); *G01N 30/02* (2013.01); *G01N 33/2823* (2013.01); *H01J 49/0027* (2013.01)

(58) Field of Classification Search
CPC ........ E21B 49/10; E21B 43/116; E21B 49/06; E21B 49/08; G01N 33/2823; G01N 11/00; G01N 30/02; G01J 3/42; G01J 3/44; G01J 3/4406; G01J 3/443; H01J 49/0027
(Continued)

(56) References Cited

U.S. PATENT DOCUMENTS 3,419,089 A * 12/1968 Venghiattis ........... E21B 43/116
166/100
3,934,468 A 1/1976 Brieger
(Continued)

FOREIGN PATENT DOCUMENTS

CA 2597809 2/2009
WO 2011/063086 5/2011

OTHER PUBLICATIONS

Russian Office Action for corresponding Russian Application Serial No. 2014110011 dated May 18, 2015; with English translation; 10 pages.
(Continued)

*Primary Examiner* — Freddie Kirkland, III
(74) *Attorney, Agent, or Firm* — Kenneth L. Kincaid

(57) ABSTRACT

Techniques for sampling a subsurface reservoir include lowering a downhole logging tool comprising one or more samplers, a cleaner system, and a sample probe bit into a borehole until at least one sampler is positioned correctly in a subterranean reservoir; advancing the cleaner system into the reservoir cleaning mud filtrate and contaminated reservoir material away into a mud column; advancing the sample probe bit into the reservoir; and solvent is injected into the reservoir from the solvent reservoir.

38 Claims, 13 Drawing Sheets

(51) Int. Cl.
*E21B 49/06* (2006.01)
*E21B 49/10* (2006.01)
*G01J 3/42* (2006.01)
*G01J 3/44* (2006.01)
*G01J 3/443* (2006.01)
*G01N 11/00* (2006.01)
*G01N 30/02* (2006.01)
*H01J 49/00* (2006.01)
*G01N 33/28* (2006.01)

(58) Field of Classification Search
USPC .......................................................... 73/863
See application file for complete search history.

(56) References Cited

U.S. PATENT DOCUMENTS

| | | | |
|---|---|---|---|
| 5,765,637 A * | 6/1998 | Dietle | E21B 33/13 166/100 |
| 6,164,126 A | 12/2000 | Ciglenec et al. | |
| 7,095,012 B2 | 8/2006 | Fujisawa et al. | |
| 7,219,541 B2 | 5/2007 | DiFoggio | |
| 7,458,257 B2 | 12/2008 | Pop et al. | |
| 7,703,317 B2 | 4/2010 | Goodwi et al. | |
| 7,966,273 B2 | 6/2011 | Hegeman et al. | |
| 8,336,370 B2 | 12/2012 | Larter et al. | |
| 8,495,921 B2 | 7/2013 | Larter et al. | |
| 8,499,831 B2 * | 8/2013 | Church | E21B 49/10 166/100 |
| 2010/0126717 A1 | 5/2010 | Kuchuk et al. | |

OTHER PUBLICATIONS

Decision to Grant for corresponding Russian Application Serial No. 2014110011 dated Jul. 17, 2015; with English translation; 17 pages.

S. Later, et al, "The origin, prediction and impact of oil viscosity heterogeneity on the production characteristics of tar sand and heavy oil reservoirs," Journal of Canadian Petroleum Technology 47, 2008, pp. 52-61.

* cited by examiner

RESERVOIR SAMPLING TOOLS AND METHODS

CROSS REFERENCE TO RELATED APPLICATION

This application claims priority to U.S. Provisional Patent Application Ser. No. 61/524,162, entitled "Reservoir Sampling Tools and Methods," filed Aug. 16, 2011, the entire contents of which are incorporated by reference as if fully set forth herein.

TECHNICAL FIELD

This disclosure relates to methods and apparatus for separating an oil and water fluid sample from an oil reservoir sample.

BACKGROUND

The bulk of the world's liquid petroleum resources are located in heavy oil and oil sand reservoirs. While some of this resource can be recovered by highly geotolerant recovery processes such as mining, these procedures are typically only economic for shallow resources, are very costly, produce high carbon dioxide emissions, use large volumes of water, and incur other environmental penalties. Most of the world's heavy oil and bitumen resource is buried too deeply to mine economically and so in situ recovery methods utilizing boreholes predominate. Conventional in situ recovery of viscous and poor quality oils currently relies on either primary production, as in cold heavy oil production, or thermal and/or solvent based methods to mobilize the oil by reducing its viscosity. Analysis of the variability of the petroleum resource may often necessitate sampling reservoirs samples at high frequency.

SUMMARY

In one general implementation, a system for sampling a subsurface reservoir includes a sampling device including a cylindrical member that includes a closed distal end and an end member that extends from the closed distal end, the end member configured to extend a first distance beyond the closed distal end and penetrate into a wall of a subterranean reservoir to a first depth; and a sampling and recovery system positioned within the cylindrical member and configured to: penetrate through the closed distal end of the cylindrical member and into the subterranean reservoir to a second depth that is greater than the first depth; and recover a sample of reservoir material or reservoir fluids from the reservoir.

In a first aspect combinable with the general implementation, the cylindrical member further includes an inner lumen, and the sampling and recovery system includes at least one of: a drill bit configured to penetrate through the closed distal end of the cylindrical member and into the subterranean reservoir to the second depth; or a cannula configured to penetrate through the closed distal end of the cylindrical member and into the subterranean reservoir to the second depth.

In a second aspect combinable with any of the previous aspects, the cannula includes a side-port cannula.

In a third aspect combinable with any of the previous aspects, the first depth is greater than a thickness of at least one of a contaminated layer coating the wall or invaded into the reservoir; and the sample is substantially free of contaminants from the contaminated layer.

In a fourth aspect combinable with any of the previous aspects, the sampling device is positionable on a tool configured to be lowered into a borehole formed in the reservoir.

In a fifth aspect combinable with any of the previous aspects, multiple sampling devices are positionable on a tool configured to be lowered into a borehole formed in the reservoir.

In a sixth aspect combinable with any of the previous aspects, the closed distal end of the cylindrical member is configured to open outwardly flower-style into the reservoir when drilled through by the sampling bit.

In a seventh aspect combinable with any of the previous aspects, the closed distal end of the cylindrical member includes an exit area which can be drilled through once the cylindrical member is drilled into the reservoir.

In an eighth aspect combinable with any of the previous aspects, the sample includes heavy oil or bitumen or reservoir water, the system further including: an extraction device configured to extract heavy oil or bitumen from the sample; and an analysis device configured to receive the extracted heavy oil or bitumen and determine one or more properties of the extracted heavy oil or bitumen.

In a ninth aspect combinable with any of the previous aspects, the extraction device extracts the heavy oil or bitumen in situ in the borehole and the analysis device determines the one or more properties of the extracted heavy oil or bitumen in situ.

In a tenth aspect combinable with any of the previous aspects, the analysis device includes a viscometer or rheometer configured to determine an absolute viscosity of the extracted heavy oil or bitumen solution.

In another general implementation a system for sampling a subsurface reservoir includes a sampling device including a cylindrical member that includes a closed distal end and an end member that extends from the closed distal end, the end member configured to extend a first distance beyond the closed distal end and penetrate into a wall of a subterranean reservoir to a first depth; a sampling tube positioned within the cylindrical member; a penetration device positioned within the sampling tube and configured to penetrate through the closed distal end of the cylindrical member and into the subterranean reservoir to a second depth that is greater than the first depth, where the distal end provides a shield from the contaminated layer; a solvent injecting device configured to extend from the sampling tube and inject a spectroscopically distinct polar solvent into the reservoir, wherein the solvent extracts a fluid sample from the reservoir; and a pump configured to withdraw fluid from the reservoir into the solvent injecting device, the fluid including the solvent and the fluid sample.

In a first aspect combinable with the general implementation, the fluid sample includes an oil sample, a water sample, or an oil and water sample.

In a second aspect combinable with any of the previous aspects, the penetration devices includes one of a drill bit or a cannula.

A third aspect combinable with any of the previous aspects further includes an analysis device operatively connected to the solvent injecting and recovery device and configured to receive the withdrawn fluid and determine one or more properties of the fluid while in situ in the reservoir.

In a fourth aspect combinable with any of the previous aspects, the analysis device includes: a spectrometer or sensor configured to determine a concentration of oil or solvent in the fluid sample; and a viscometer configured to determine a viscosity of the oil in the fluid sample.

In a fifth aspect combinable with any of the previous aspects, the analysis device includes a viscometer configured to determine a viscosity of oil in the fluid sample.

In a sixth aspect combinable with any of the previous aspects, the analysis device includes a spectrometer or sensor configured to determine the spectral properties of the reservoir fluid solution and a concentration of oil in the fluid sample.

In a seventh aspect combinable with any of the previous aspects, the analysis device includes a spectrometer configured to determine the spectral properties of the reservoir fluid solution.

In an eighth aspect combinable with any of the previous aspects, the analysis device includes a spectrometer configured to determine the spectral properties of the reservoir fluid solution and a concentration of water in the fluid sample.

In a ninth aspect combinable with any of the previous aspects, the solvent injecting device includes a sampling bit configured to screw into the reservoir.

In another general implementation, a method performed with either of the systems of the previous general implementations includes in response to drilling the sampling bit through the closed distal end of the cylindrical member, the distal end opens outwardly flower-style into the reservoir.

A first aspect combinable with the general implementation further includes, in response to drilling the sampling bit through the closed distal end of the cylindrical member, the sampling bit drills through a soft metal or polymer end component.

A second aspect combinable with any of the previous aspects further including determining a property of the fluid sample. The property may include at least one of: a viscosity of a heavy oil or bitumen extracted from the fluid sample; an oil saturation of the heavy oil or bitumen extracted from the fluid sample; a water saturation in the reservoir; an API of the heavy oil or bitumen extracted from the fluid sample; a gas oil ratio (GOR) of the heavy oil or bitumen extracted from the fluid sample; a formation volume factor or other PVT parameter of the heavy oil or bitumen extracted from the fluid sample; a TAN of the heavy oil or bitumen extracted from the fluid sample; a pourpoint of the heavy oil or bitumen extracted from the fluid sample; or a Conradson carbon of the heavy oil or bitumen extracted from the fluid sample.

In a third aspect combinable with any of the previous aspects, determining a property includes determining the property using multivariate analysis of one or more spectral responses.

In a fourth aspect combinable with any of the previous aspects, the one or more spectral responses include one or more responses based on mass or light-based spectroscopy, one or more responses from an electronic nose, or one or more responses based on non-spectroscopic sensors.

In a fifth aspect combinable with any of the previous aspects, determining a property includes determining the property in situ in the borehole.

In a sixth aspect combinable with any of the previous aspects, determining a property includes determining the property at a terranean surface after removing the fluid sample from the borehole.

A seventh aspect combinable with any of the previous aspects further includes determining a concentration in the oils of crude oil components including alkanes or aromatic hydrocarbons using multivariate analysis of the spectral responses.

An eighth aspect combinable with any of the previous aspects further includes assessing at least one of a plurality of reservoir compartments or intra reservoir barriers using concentrations of at least one of saturated hydrocarbons, aromatic hydrocarbons, or thioaromatic compounds.

In a ninth aspect combinable with any of the previous aspects, the aromatic hydrocarbons or thioaromatic compounds include at least one of alkylbenzenes, alkylnaphthalenes, alkylbenzothiophenes, alkyldibenzothiophenes, or alkylphenanthrenes.

A tenth aspect combinable with any of the previous aspects further includes extracting an oil sample from the reservoir using a hydrophobic solvent.

An eleventh aspect combinable with any of the previous aspects further includes extracting a water sample from the reservoir using a hydrophilic solvent.

A twelfth aspect combinable with any of the previous aspects further includes extracting a combined oil and water sample from the reservoir using a mixture of a hydrophobic and a hydrophilic solvent.

A thirteenth aspect combinable with any of the previous aspects further includes extracting a combined oil and water sample from the reservoir using a mixture of dichloromethane and methanol.

A fourteenth aspect combinable with any of the previous aspects further includes at least one of: extracting an oil sample from the reservoir using at least one of hexane, toluene, dichloromethane (DCM), chloroform, carbon tetrachloride, or carbon disulfide; or extracting an oil sample from the reservoir using an isotopically-labeled hydrocarbon that has distinctive spectrometric properties different from those of crude oils.

A fifteenth aspect combinable with any of the previous aspects further includes extracting a water sample from the reservoir using at least one of a single alcohol, a mixture of alcohols, or a ketone that have distinctive spectrometric properties different from those of water.

In another general implementation, a method includes: selecting an analytical method; analyzing a suite of calibration oils; and analyzing samples of the suite of calibration oils for chemical composition using a sensor system.

In a first aspect combinable with the general implementation, the selected method is capable of distinguishing chemical compositional differences in crude oils necessary to assess viscosity by chemical proxy.

In a second aspect combinable with any of the previous aspects, selecting an analytical method includes at least one of: assessing at least one of a chemical compound type or a molecular weight difference based on an oil composition; or identifying and tracking geochemical processes or properties that control oil viscosity.

In a third aspect combinable with any of the previous aspects, the geochemical processes include petroleum biodegradation, oil source properties, or maturity.

A fourth aspect combinable with any of the previous aspects further includes determining viscosity data to provide a multivariate transform that converts geochemical results into viscosities using at least one of multivariate statistics or neural network analysis.

A fifth aspect combinable with any of the previous aspects further includes geochemically analyzing oils extracted from target core or cuttings samples.

A sixth aspect combinable with any of the previous aspects further includes converting results from the geochemical analysis via the multivariate transform function to a viscosity (or other fluid property estimate).

In a seventh aspect combinable with any of the previous aspects, dead oil viscosity measurements are used as calibration data (e.g., when viscosity is to be estimated).

In an eighth aspect combinable with any of the previous aspects, live oil viscosity measurements are used as calibration data (e.g., when viscosity is to be estimated).

In a ninth aspect combinable with any of the previous aspects, the sensor system includes at least one of: a mass sensor; an infrared sensor; a UV sensor; a gas chromatography or GC-MS based system; an ion mobility MS system; an optical spectroscopy system; an electronic nose system; a Raman spectroscopy system; a laser-induced fluorescence spectroscopy system; a cavity ring down laser absorption spectroscopy system; or a resonance ionization spectroscopy system.

In a tenth aspect combinable with any of the previous aspects, the sensor is an infrared sensor and a matrix of properties of the oil or bitumen are the effective absorbance or transmission of the oil solution in solvent at various far or near infrared wavelengths.

In an eleventh aspect combinable with any of the previous aspects, the sensor is a mass spectrometer, and the oil or bitumen properties are the relative peak heights at various molecular masses.

In a twelfth aspect combinable with any of the previous aspects, the sensor is an electronic nose and the data spectrum includes of a set of responses from each sensor element, each element responding to a suite of specific component types.

In a thirteenth aspect combinable with any of the previous aspects, sensor elements may be chosen to be sensitive to specific oil components that are known proxies for viscosity or other fluid property to be assessed.

In a fourteenth aspect combinable with any of the previous aspects, the oil components include at least one of light hydrocarbons C1-C5, intermediate hydrocarbons C6-C11, or C12-C40 hydrocarbons.

In a fifteenth aspect combinable with any of the previous aspects, the oil components include specific indicators of biodegradation level; or specific alkanes and aromatic hydrocarbons including specific alkylaromatic compounds.

In a sixteenth aspect combinable with any of the previous aspects, the specific indicators of biodegradation level include an indication of asphaltene, resin or thioaromatic compounds.

In another general implementation, a method includes lowering a downhole logging tool including one or more samplers, a cleaner system, and a sample probe bit into a borehole until at least one sampler is positioned correctly in a subterranean reservoir; advancing the cleaner system into the reservoir cleaning mud filtrate and contaminated reservoir material away into a mud column; advancing the sample probe bit into the reservoir; and solvent is injected into the reservoir from the solvent reservoir.

In a first aspect combinable with the general implementation, the sample probe bit is advanced by drilling through a plastic or soft metal end plate of a filtrate cleaner of the cleaning system.

In a second aspect combinable with any of the previous aspects, the one or more samplers includes between 10-20 samplers.

In a third aspect combinable with any of the previous aspects, during positioning, the sampler is sealed from the borehole environment by a metal or plastic seal.

A fourth aspect combinable with any of the previous aspects further includes injecting the solvent using an electric, dual piston, piston pump that both supplies and withdraws solvent via tubes and holes in the sample bit.

In a fifth aspect combinable with any of the previous aspects, injecting the solvent includes injecting the solvent into one or both holes or flowed from one hole via the reservoir to the other.

A sixth aspect combinable with any of the previous aspects further includes flowing the solvent back through the sample bit to an analytical sensor.

A seventh aspect combinable with any of the previous aspects further includes examining, with the sensor, the sample at reservoir pressure and temperature maintained across a polymer membrane via an environmental equalization port.

An eighth aspect combinable with any of the previous aspects further includes sealing or storing the sample recovered with solvent in a sampling container.

In a ninth aspect combinable with any of the previous aspects, the sampling container is sealed with electrically rotated valves.

A tenth aspect combinable with any of the previous aspects further includes recording and storing analytical data from the sensor in an electronic data model.

An eleventh aspect combinable with any of the previous aspects further includes retracting the sampler into the tool and positioning a new sampler.

Various implementations of a system for reservoir sampling according to the present disclosure may include one or more of the following features and/or advantages. For example, the system may permit in situ sampling heavy oils and bitumens that do not flow naturally from a reservoir into a wellbore. The system may also provide for more accurate sampling by, for instance, cleaning a borehole wall prior to sampling, thereby permitting clean samples to be obtained under in situ conditions. In another example, solvent recovery of oil (and water) from reservoirs may obtain in situ fluid data and (at least partially) overcome problems associated with using flow based sampling tools in heavy oil and bitumen reservoirs where fluids may not flow. Further, both chemical (proxy-based) correlation methods and direct solvent mixture-based in situ viscosity measurement methods can then be used to derive reliable viscosity or other fluid property measurements.

These general and specific aspects may be implemented using a device, system or method, or any combinations of devices, systems, or methods. The details of one or more implementations are set forth in the accompanying drawings and the description below. Other features, objects, and advantages will be apparent from the description and drawings, and from the claims.

DETAILED DESCRIPTION

Figure 1:
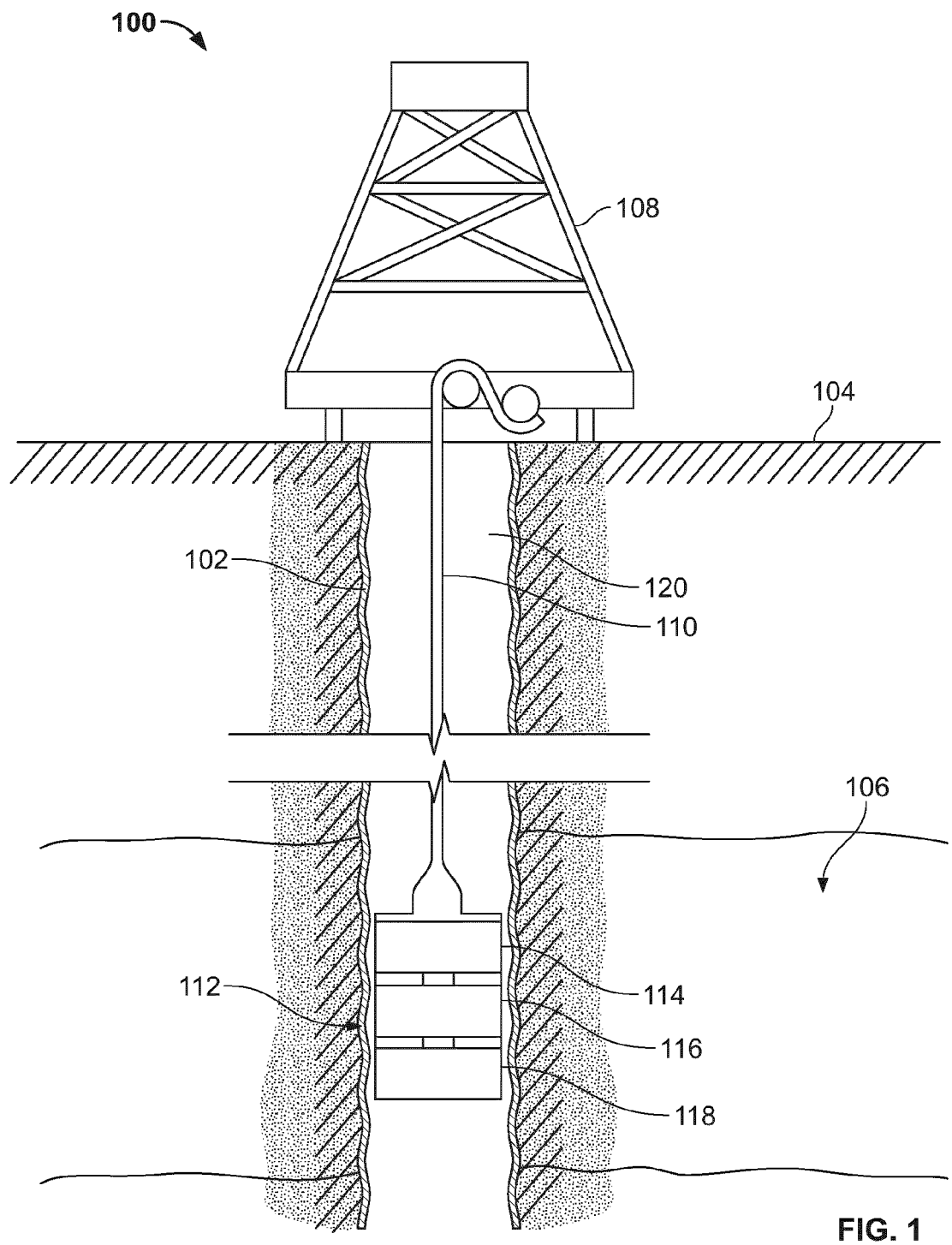
FIG. 1 illustrates an example downhole (e.g., in situ) system having a sampling device, an extraction device, and an analysis device.

The present disclosure discusses the recovery of oil or bitumen and the determination of the viscosity of bitumen and heavy oils in situ in the drill hole and in real time at the well site. The measurement of oil viscosity in situ may be preferable to surface measurements because it precludes most of the problems associated with sample degradation, especially volatile and solution gas loss during sample recovery, transportation, storage, laboratory preparation and analysis. In this disclosure, a sampling system and analytical device for determining oil viscosity from a solvent recovered oil is described. The oil viscosity or other property can be determined under in situ conditions of pressure and temperature in the subsurface or at surface conditions in a lab or elsewhere including at rig side.

Petroleum flow in a reservoir is controlled by natural or induced fluid potential gradients and the fluid mobility in the reservoir. For heavy oil and bitumen, variations in the mobility ratio, defined as the ratio of the permeability of a reservoir to oil, divided by oil viscosity is the key parameter in controlling production. In heavy oil and bitumen reservoirs, oil mobility is controlled by oil viscosity variations to a larger extent than in conventional oil reservoirs where permeability variations commonly dominate oil mobility variation.

The relative permeability of a reservoir to oil depends on several factors but principally is related to the oil saturation in the reservoir (So). Oil phase viscosity in heavy oilfields is a function of the independent parameters of (1) the original oil quality or genetic character; (2) the extent of biodegradation; and (3) the addition and mixing of a late, second charge of oil to the reservoir. In heavy oil reservoirs, oil viscosities commonly vary by orders of magnitude across the thickness of a reservoir, or laterally over even the distance of a single horizontal production well. These substantial variations are often not taken into account (e.g., oil phase viscosity is often assumed constant throughout the reservoir) when designing the operating strategy or well placement for recovery processes, even though these variations can have significant effects on production. This is due to the difficulty of adequately measuring these variations. The poor recoveries and inaccurate prediction of production targets seen in many current thermal or cold recovery operations may be partly related to disregarding the natural variation in oil quality in heavy oil and bitumen reservoirs when designing and optimizing production strategies.

In highly compositionally graded heavy oil and bitumen reservoirs, proper consideration of fluid property variations, in addition to comprehensive characterization of reservoir properties, can facilitate geotailored design of recovery methods, including well placement and optimization production strategies, for each reservoir to lower operational costs and improve recovery of these viscous oils. Determination of the oil absolute viscosity and the viscosity variation as a function of position in the reservoir (vertical and lateral) in real time will allow for decisions to be made in real time, while the rig is in position at the well site. Onsite viscosity and fluid saturation determinations of heavy oils and bitumen allow several different field operations to be undertaken: (1) decisions as to whether or not well testing to recover production data or fluid samples is likely to be successful can be made based on real fluid data generated in real time at the well site; (2) decisions on where to place a horizontal well segment can be made from the analysis of fluid property variations from a vertical well segment facilitating cold production well locations at the well site while the rig is still onsite; (3) the most accurate viscosity data possible is obtainable without sample storage and processing artifacts; and (4) live oil viscosity data is available to aid in design of recovery processes and surface facilities design.

In heavy oil or bitumen reservoirs, oil phase viscosity may vary by as much as two orders of magnitude over a vertical reservoir thickness of <50 m. The magnitude of the variation of viscosity approaches or exceeds the variation in permeability in many reservoirs. While thermal operations reduce viscosity and viscosity gradients in heavy oil reservoirs, viscosity gradients are not negligible, even at steam temperature and thus accurate assessment of oil viscosities and relative permeabilities at process conditions is necessary for making reliable field development decisions and optimizing the production engineering approaches to development strategy, including well placement. These factors require the availability of high quality viscosity data at a vertical resolution between data points of less than 5 m. Thus seismic or other surface based methods with much larger spatial resolution will be limited to providing bulk rather than spatially resolved reservoir characteristics.

Figure 6:
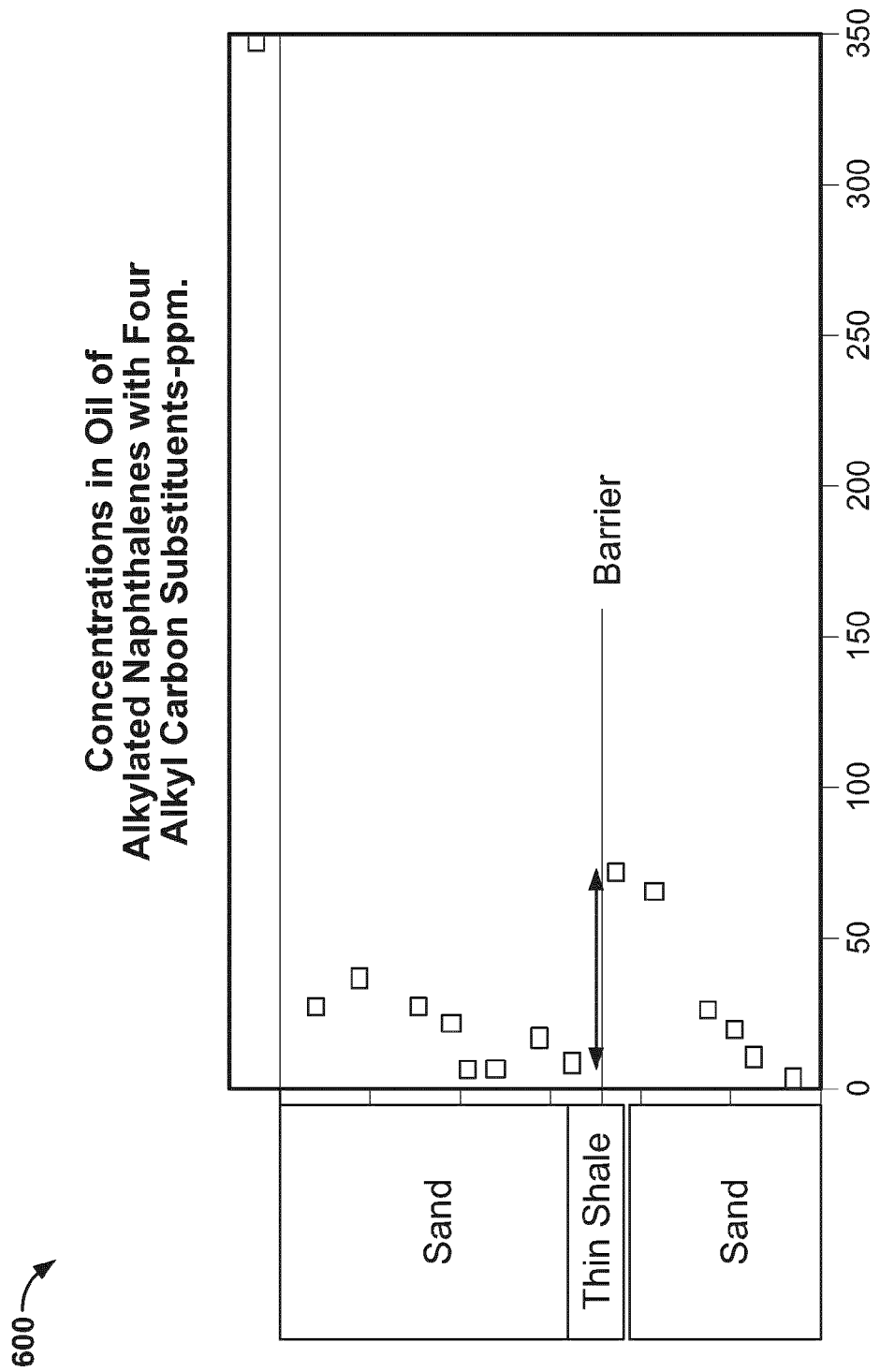
FIG. 6 illustrates geochemical steps in the depth versus concentration profile of alkylaromatic hydrocarbons obtained from analysis of rock samples in a heavy oil reservoir indicate a hydrodynamic barrier due to shale or other low permeability horizon.

The economic viability of various heavy oil and bitumen development strategies are strongly affected and potentially controlled by oil viscosity, but also by the presence of effective fluid flow (hydrodynamic) barriers within a reservoir. Petrophysical logs (e.g., gamma ray, resistivity) may indicate the presence of a shaley layer, carbonate cemented layer or other potential barrier within a reservoir where it intersects the borehole, but logs cannot be used to determine whether this stratigraphic layer is an effective fluid migration barrier with low effective permeability over an extensive lateral area. On the other hand, reversals or steps in the depth related logs of chemical and/or physical properties of the heavy oil or bitumen in a high resolution vertical profile can indicate the presence of a barrier or baffle to fluid flow regardless of whether or not such a barrier is visible or apparent in petrophysical logs or otherwise. For example, FIG. 6 shows geochemical steps in the depth versus concentration profile of alkylaromatic hydrocarbons obtained from analysis of rock samples in a heavy oil reservoir indicate a hydrodynamic barrier due to a thin shale or other low permeability horizon.

Over geological time periods, an inability to mix fluids across a true barrier will result in a compositional step when different oils are charged to the different compartments or when biodegradation alters oils differentially in one compartment compared to another. Real time detection of effective fluid flow barriers requires a detailed knowledge of the chemistry of the oil or bitumen and/or high quality oil viscosity determinations with a spatial sampling resolution of at least about 1 to 5 m vertically and every 50 to 100 m laterally if in a horizontal well. While such approaches are applied on core based analyses, real time in situ analysis of such compositional steps would be a substantial advance and the method described here would permit that. While FIG. 6 shows a substantial compositional step in alkylnaphthalene concentrations, in other settings other compounds can be used, selected on the basis that concentration variations are substantial across the reservoir, and in some cases statistical methods of comparing oil compositions across putative compartment boundaries (e.g., t tests for example) could be employed. To generate such profiles, spot analyses of many samples in situ is necessary.

FIG. 1 illustrates an example downhole (e.g., in situ) system 100 having a downhole tool 112 with a sampling device 114, an extraction device 116, and an analysis device 118. As illustrated in this figure, a wellbore 102 defines a borehole 120 from a terranean surface 104 to one or more subterranean zones 106 (e.g., geologic formations and/or reservoirs) and provides easier and more efficient production of any hydrocarbons located in such subterranean formations. A drilling assembly 108 (a portion of which is illustrated) may be used to form the borehole 120 extending from the terranean surface 104 and through one or more geological formations in the Earth. Although illustrated as and referred to as a terranean surface 104, in some embodiments, the terranean surface 104 may be an ocean, gulf, sea, or any other body of water under which petroleum-bearing formations may be found. In short, reference to the terranean surface 104 includes both land and water surfaces and contemplates forming and/or developing one or more wellbores 102 from either or both locations.

In some embodiments of the system 100, the wellbore 102 may be cased with one or more casings (not shown). For example, the wellbore 102 may include a conductor casing that extends from the terranean surface 104 shortly into the Earth; a surface casing that may enclose a slightly smaller borehole (relative to the conductor casing) and protect the wellbore 102 from intrusion of, for example, freshwater aquifers located near the terranean surface 104; and a production casing that may enclose an even smaller borehole (relative to the surface casing) and provide an enclosed path for the circulation of fluid (e.g., hydrocarbon fluids) from the subterranean zone 106 to the terranean surface 104.

Although shown as a substantially vertical wellbore 102, in some embodiments, the wellbore 102 may be offset from vertical (e.g., a slant wellbore). Even further, in some embodiments, the wellbore 102 may be a stepped wellbore, such that a portion is drilled vertically downward and then curved to a substantially horizontal wellbore portion. The substantially horizontal wellbore portion may then be turned downward to a second substantially vertical portion, which is then turned to a second substantially horizontal wellbore portion. Additional substantially vertical and horizontal wellbore portions may be added according to, for example, the type of terranean surface 104, the depth of one or more target subterranean formations 106, the depth of one or more productive subterranean formations, and/or other criteria.

The downhole tool 112 may be lowered into the wellbore 102 by a conductor 110. Conductor 110 may be, for example, a single-strand or multistrand wire or cable such as a wireline, slickline, or other electrical conductors. Conductor 110 may also be, for instance, tubing such as coiled tubing or other form of a continuous length of pipe wound on a spool that includes an electrical conductor or hydraulic conduit.

The illustrated downhole tool 112 includes the sampling device 114, the extraction device 116, and the analysis device 118. Although illustrated as a single "tool," one or more of the components 114, 116, and 118 may be a separate downhole component or may be grouped with other downhole tools, such as, for instance, a bottom hole assembly, logging tool, MWD tool, or other downhole tool.

At a high level, the sampling device 114 may be operated to remove a portion of the subterranean zone 106 (e.g., a core sample, a fluid sample, or other piece of the zone 106) and receive the portion into the tool 112 for further analysis. For example, once taken, one or more fluids or other pieces may be extracted from the sample with the extraction device 116 and analyzed by the analysis device 118 as further described with reference to FIGS. 2A-2E, 3A-3B, 4, 5, 9, and 10.

FIGS. 2A-2E illustrate views of an example sampling device 114 described above with reference to FIG. 1. With reference to these figures, the sampling device 114 includes a housing 124 that at least partially encloses a cylindrical member 126 that is coupled to a motor 138. A closed end 140 of the cylindrical member 126 may be located opposite the motor 138 and may include a drill bit (e.g., a masonry or high speed steel type drill bit) extending from the cylindrical member 126. As illustrated, the closed end 140 may be curved or concave, but may also be relatively straight. Enclosed within the cylindrical member is an auger 134 coupled to an auger motor 136 and a sampling tube 130 that may be sized to be just smaller than an inner dimension (e.g., diameter) of the cylindrical member 126. Further, a moveable brace 132 (e.g., an extendable brace) may be coupled to or integral with the housing 124 opposite the closed end 140 of the cylindrical member 126.

In operation, and with reference to FIGS. 2A-2E, the sampling device 114 may, at a high level, contact and clean a surface of the wellbore 102, extend a sampler (e.g., the auger 134) through a contaminated layer 122 of the wellbore 102 and into the subterranean zone 106, extract a portion of the zone 106 back into the device 114, and prepare the portion (e.g., a sample 146) for further extraction and analysis.

Figure 2A:
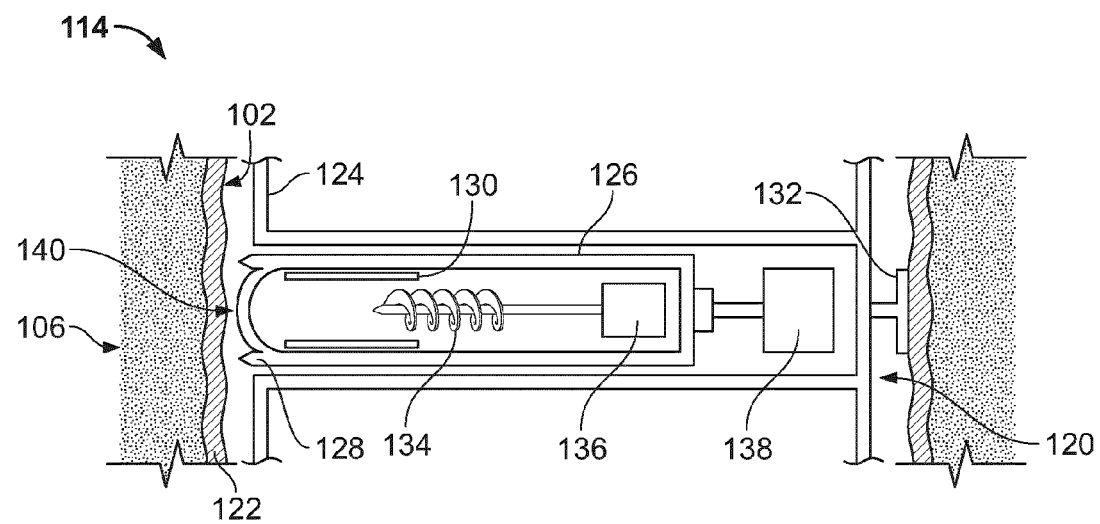
FIGS. 2A-2E illustrate views of an example sampling device during operation of same.

For example, FIG. 2A shows the sampling device 114 at a particular location within the wellbore 102 (e.g., downhole) and adjacent to the subterranean zone 106 (or any other formation or reservoir to be sampled). As shown in FIG. 2A, the auger 134 is enclosed within the cylindrical member 126 and the auger 134 and cylindrical member 126 itself are in a retracted state. As illustrated the brace 132 may be extending (or extended) to contact the wellbore 102 and, for example, stabilize a position (e.g., vertical, radial) of the sampling device 114 in the borehole 120.

Figure 2B:
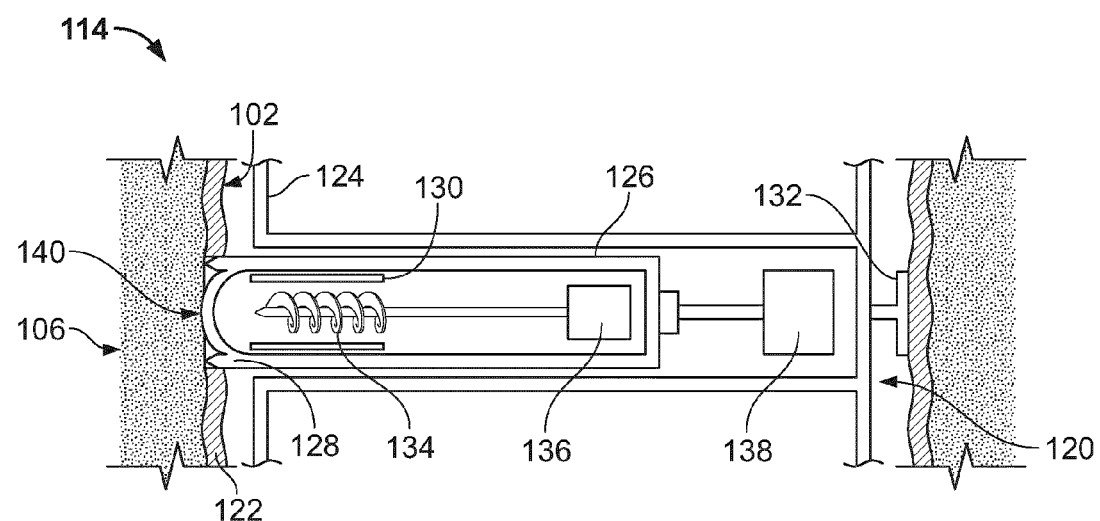

Turning to FIG. 2B, this figure illustrates the cylindrical member 126 extended by the motor 138 from its retracted state so that the wall cleaner drill bit 128 is in contact with the wellbore 102. In some embodiments, the drill bit 128 may be rotated (e.g., by the motor 138) to remove at least a portion of the contaminated layer 122 of the wellbore 102, thereby cleaning the zone 106 prior to sampling. As further illustrated in FIG. 2B, the auger 134 may be at least partially extended from the retracted position by the auger motor 136 in this state to be closely adjacent the closed end 140.

Figure 2C:
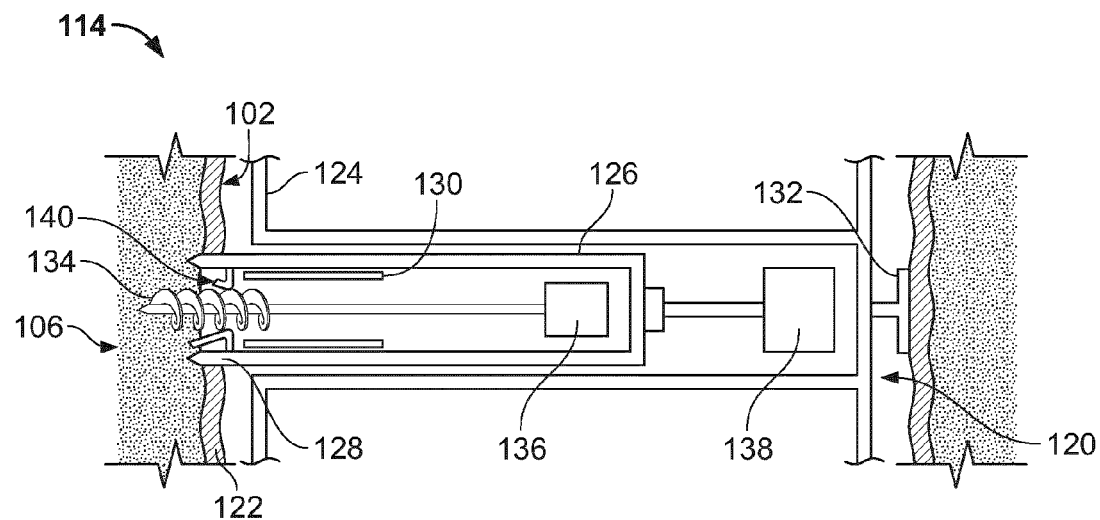

Turning to FIG. 2C, this figure shows the auger 134 in an extended position after it has broken through the closed end 140 and drilled through the contaminated layer 122 and into the subterranean zone 106. In some embodiments, the auger 134 may be extended (e.g., forcibly) by the auger motor 136 into the formation of the zone 106 and then rotated (e.g., by the motor 136) in order to remove a portion of the formation for later analysis. As illustrated, the sampling device 114 may be held relatively stable through the brace 132 in contact with the wellbore 102 and/or the drill bit 128 portion of the cylindrical member 126 in contact with the wellbore 102.

Figure 2D:
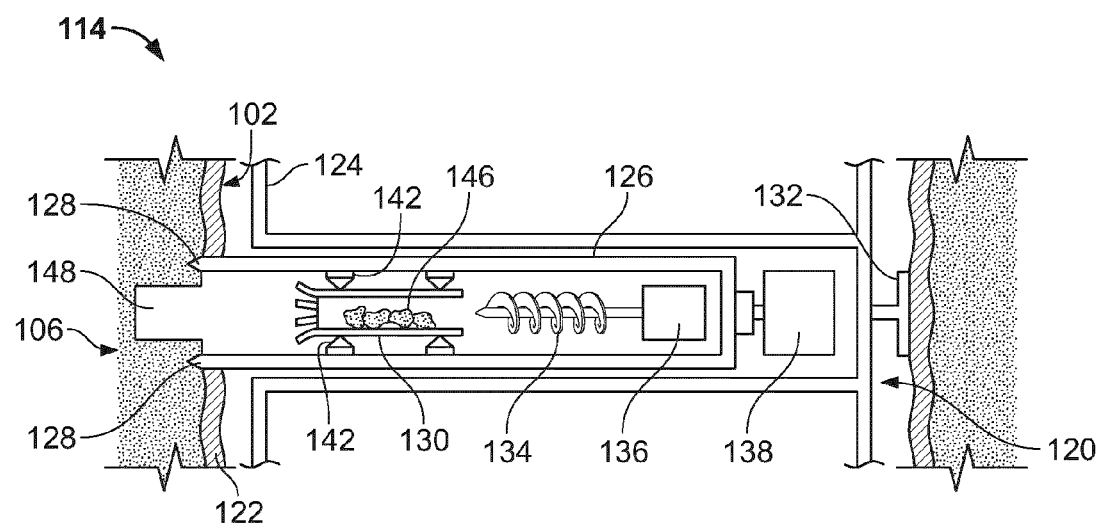

Turning to FIG. 2D, this figure illustrates a portion of the formation of the zone 106 removed, with a hole 148 left in the zone 106. As illustrated, the cleaner bit section 128 remains in the formation sealing off the sampler from drilling fluids. In alternative implementations, the cleaner bit section 128 may be withdrawn, e.g., prior to sealing off the sampler from drilling fluids.

The sample 146, as illustrated, is withdrawn from the formation into the sampling tube 130 by the auger 134, which returns to its retracted position (e.g., by the motor 136). As further illustrated, the cylindrical member 126 is withdrawn to its retracted position by the motor 138. As illustrated in this figure, the sampling tube 130 includes a flower-style opening to receive the sample 146 there through. Once received into the sampling tube 130, the sample 146 may be at least partially enclosed therein by constricting ends of the tube 130 by crimping devices 142.

Figure 2E:
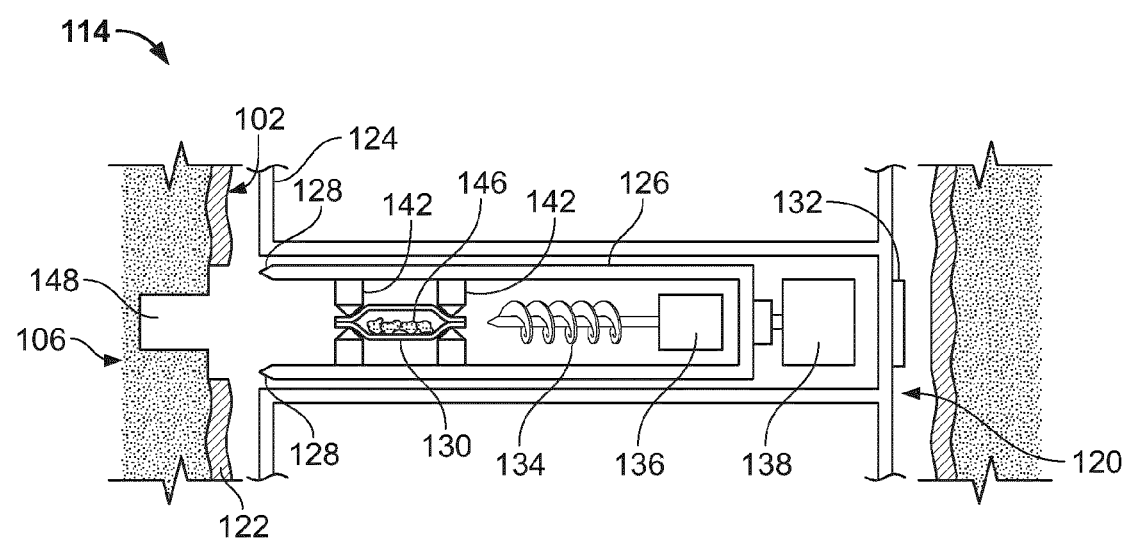

Turning to FIG. 2E, this figure illustrates the sample 146 at least partially enclosed within the sampling tube 130 and prepared for further analysis (e.g., via the extraction device 116 and analysis device 118). As illustrated, the crimping devices 142 pinch ends of the sampling tube 130 to at least partially enclose the sample 146 within the tube 130. As explained more fully below, the sample 146 may be passed to the extraction device 116 within the enclosed sampling tube 130. As illustrated in FIG. 2E, the wall cleaner bit 128 has been withdrawn after sample sealing in tube 130, and the brace 132 has been retracted to permit moving the tool in the wellbore. Further, the brace 132 is illustrated in FIG. 2E as withdrawn from contact with the wellbore 102, thereby allowing the device 114 to be moved in the borehole 120.

Figure 3A:
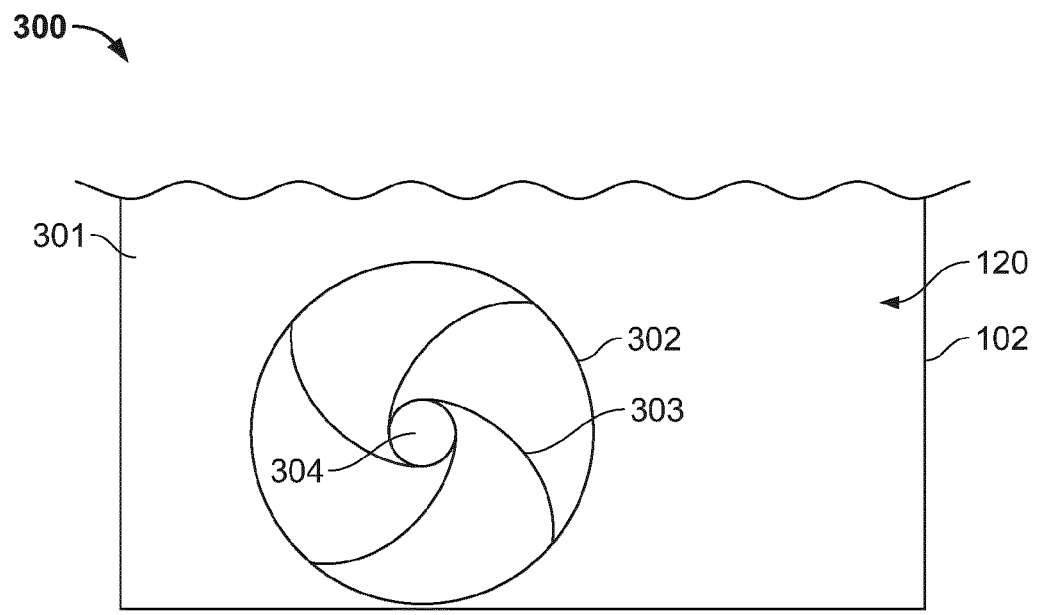
FIGS. 3A-3B illustrate a schematic of an example reservoir fluid recovery and analysis system.
Figure 3B:
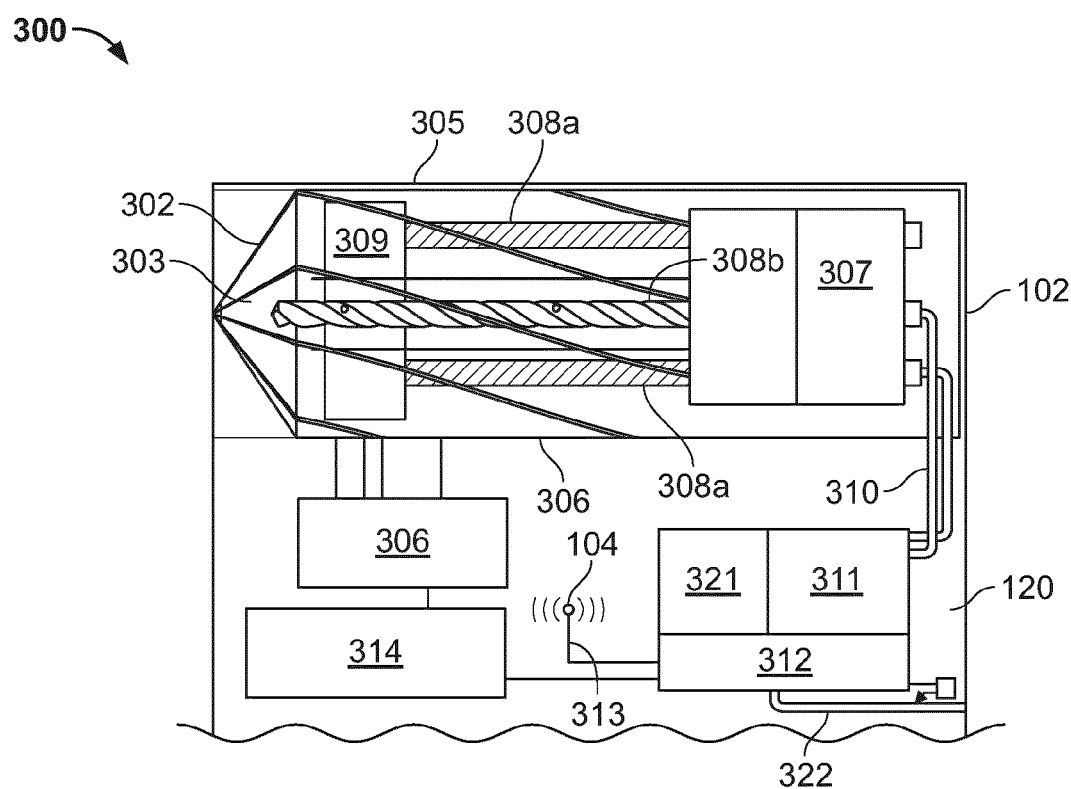

FIGS. 3A-3B illustrate views of a schematic of an example reservoir fluid recovery and analysis system 300. As illustrated, a basic tool assembly may consist of a reservoir fluid sample retrieval system; an oil and water sample recovery system; an analytical system to characterize the recovered fluids; data transmission and processing capabilities; and a sample archive system and storage for waste solvent material. The sampling system does not recover reservoir rock material or rely on flow of reservoir fluids. The sampling system operates once with additional samples being taken with replicated sampling devices stacked in the tool. The basic borehole wall cleaning and sample probe system could be modified to include a coring system or other solid material sampling system but that is not described here.

Figure 4:
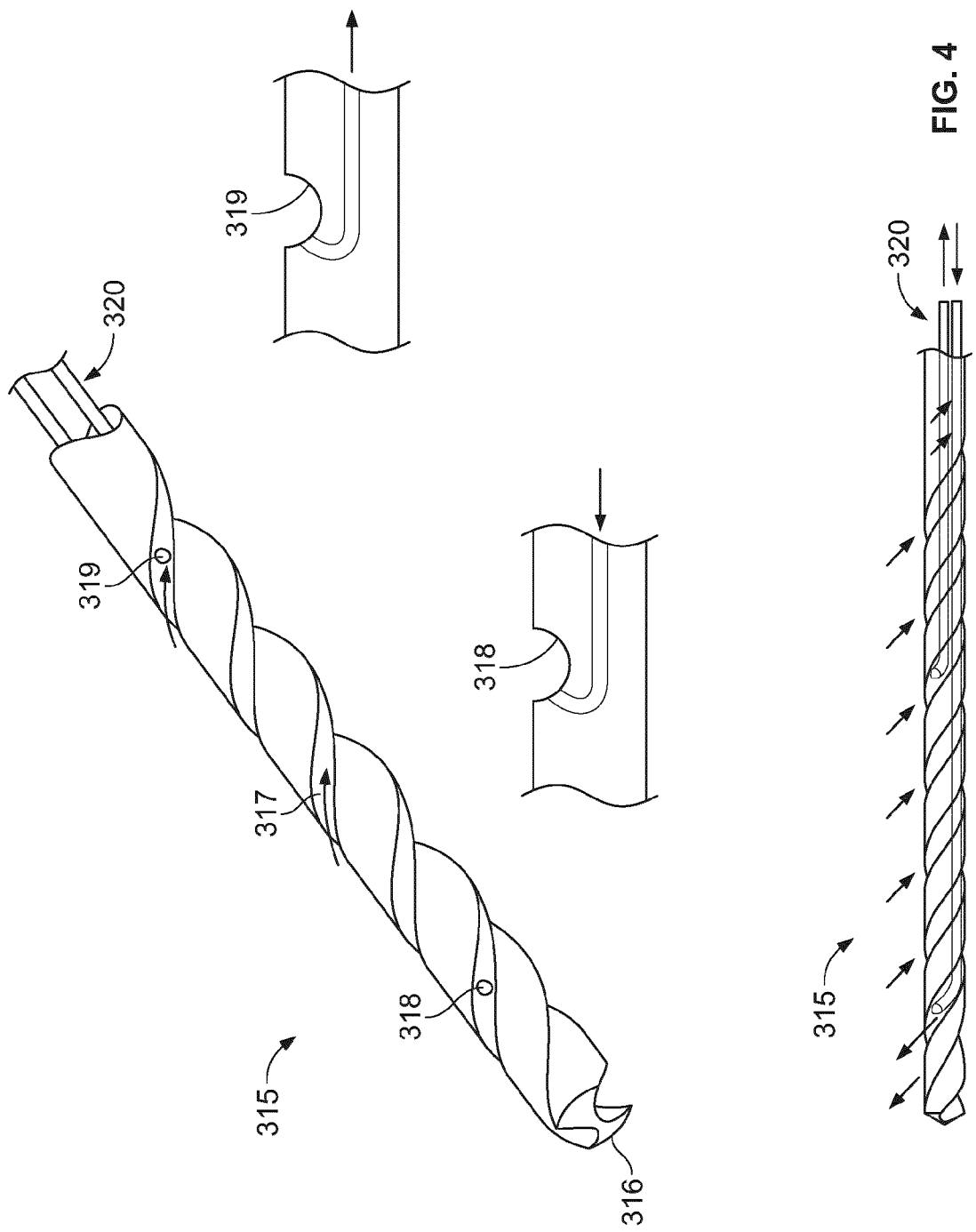
FIG. 4 illustrates a continued schematic of the example reservoir fluid recovery and analysis system showing the sampling bit system.

The system 300 shown schematically in FIGS. 3A-3B and 4 consists of a wellbore cleaning subsystem and a solvent injection and recovery probe together with an analytical subsystem and a sample recovery container. As shown, the system 300 includes a logging tool body 301, an end view of filtrate cleaner 302, cleaner ribs 303, a soft exit area for sampler probe 304, a filtrate cleaner body 305, a motor 306 to advance the filtrate cleaner body into the reservoir and rotate cleaner body, a motor 307 to spin the sample probe bit and advance probe into reservoir along advance rails, advance rails 308a to guide a sample bit 308b into a reservoir; a rail guide and support 309 for the sample probe, tubing 310 to circulate solvent to and from the probe, a pump system 311 to deliver and recover solvent from the probe (also including a solvent tank, not shown), an analytical chemical sensor system 312, a data communication system 313, a control and data processing electronics 314, and in FIG. 4, details of the sample bit 308b are shown. FIG. 4 shows an example sample bit probe 315, a bit 316, bit grooves and solvent tracks 317, a solvent delivery hole 318, a solvent recovery hole 319, solvent and fluid solution delivery tubes 320, an optional sample recovery container 321, and an isolated pressure equalization port 322 to maintain analytical chamber and fluids at reservoir pressure and temperature are shown on FIG. 3B.

Turning back to FIGS. 3A-3B and 4, a hardened steel bit end (5-10 mm in diameter) drills into the reservoir and solvent is circulated from the sampling holes in the bit and then taken back into the instrument via the tubes in the bit itself. Sample hole plugging by reservoir material can be stopped by circulating some solvent as the bit advances. Mud is kept out of the reservoir sampling environment by the filtrate cleaner body 305 which has been advanced into the formation. Several other designs for injecting, circulating and recovering solvent with oil, water, oil and water together are also possible some involving single drilled sample probes others involving two drill probes or, as described below, syringe and cannula based systems. During penetration of the reservoir, an electric motor 307 simultaneously spins the sample probe bit and advances it by helical gear rails 308.

One technique to recover fluid samples from reservoirs in which flow of fluids from reservoirs is restricted or not possible due to high oil viscosities, low reservoir permeabilities or low oil saturations is to solvent extract the reservoir. Solvents can recover oil or water or both oil and water along with their dissolved gases. Conventional drilling techniques tend to leave a residue of drilling mud filtrate at the borehole wall that may contaminate the reservoir by mud fluid flow into the reservoir. These potential contamination issues can be resolved by the presently disclosed embodiments in at least two ways. Firstly major contamination is mechanically removed by the sampling system. Secondly the chemometric approach used to assess sample fluid properties in situ depends on monitoring specific chemical proxy signals in the sample and these can be chosen to avoid chemical imaging of contaminants, permitting fluid property assessment even in contaminated samples.

The solution to cleaning the mud filtrate from the borehole wall and to remove the contaminated layers of reservoir is a blank ended or bit shaped filtrate cleaner bit 302 ("FCB") in which a false bit made of aluminum or other soft metal or fiber glass composite material or a hard plastic is rotated and moved into the borehole sweeping away drilling mud filtrate and the outer layers of the unconsolidated or soft reservoir material before the actual sampling device is drilled through the end of the filtrate cleaner bit into the formation where a sample is subsequently taken. The bit end 304 could also be manufactured to open flower-petal-style when the sampling tube is drilled into the reservoir or contain a soft segment through which the sampling system can be easily placed or drilled through after the cleaning process has occurred. This will prevent fouling of the sampling tube with metal or plastic. The FCB is simultaneously rotated and advanced slowly into the borehole by an electric motor and gearing 306.

A practical means of recovering oil or bitumen samples for viscosity assessment is to solvent extract the oil sample from the reservoir with a solvent based oil recovery system.

By choosing a dual or more complex solvent system containing both apolar and polar solvents both oil and water could be extracted quantitatively together or separately. Mixtures of dichloromethane with methanol and/or acetone can function in this way to get representative samples of both oil and water. The method is applicable both to surface (core, cuttings samples) and subsurface fluid recovery and characterization procedures.

FIG. 5 shows an example method 500 for operation of the system 300 and/or other systems described herein that are similar to the system 300. In step 502, a downhole logging tool containing one or more, and likely 10 to 20, sampler systems (e.g., sampling device 114) is lowered into the borehole until one sampler is positioned correctly in the reservoir. During positioning, the sampler is sealed from the borehole environment by a metal or plastic seal.

In step 504, the cleaner system (e.g., drill bit 308b) is advanced into the reservoir to clean mud filtrate and contaminated reservoir material away into the mud column. In step 506, the sample probe bit (e.g., bit 308) is then advanced by drilling through the plastic or soft metal end plate (e.g., closed end 140) of the filtrate cleaner (e.g., cleaner 304) into the reservoir.

In step 508, solvent is injected into the reservoir from the solvent reservoir using, e.g., an electric, dual piston, piston pump (e.g., pump 311) that both supplies and withdraws solvent via tubes and holes in the sample bit (e.g., tubes 318 and holes 319 and 320. Solvent can be injected into one or both holes or flowed from one hole via the reservoir to the other. Solvent selection is described below. Solvent is then flowed back through the sample bit to the analytical sensor (e.g., sensor 312), which examines the sample at reservoir pressure and temperature maintained across a polymer membrane via an environmental equalization port (e.g., port 322).

In step 510, the sample recovered with solvent is sealed or stored in a small steel sampling container (e.g., container 321), which is sealed with, e.g., electrically rotated valves. Analytical data from the sensor is recorded and stored in the electronic data model (e.g., model 314) or transmitted to a terranean surface. Borehole pressure and temperature data can also be recorded (devices not shown). The sampler may then be retracted into the tool and a new sampler is positioned elsewhere in the hole. Each sampler is used only once. Spectral data from each sampler is processed on board or on the surface to obtain fluid property information. The electronics, pumps, solvent handling systems and sensor system are separated from the corehole cleaner and sample probe by a sealed metal wall.

The sensor system 312 can also incorporate or be replaced with a moving filament, resonance or capillary viscometer. By varying the solvent content of the reservoir fluid solution, for example by adding more solvent in aliquots to the reservoir fluid extract and remeasuring solution viscosity, an accurate measured viscosity can be made directly and the true petroleum fluid viscosity can be obtained using the GVisc™ method described in Canadian patent application 2,597,809.

In situ determination of oil property profiles of parameters such as viscosity, API gravity or Total Acid Number (TAN) is particularly useful but cannot currently be done for bitumen reservoirs or other reservoirs where the oil does not flow to the logging tool naturally. The level of accuracy for the determination of in situ live or dead oil viscosity must be much better than a factor of 2× of the true value to make reliable well placement decisions in the field or to detect fluid flow barriers by using steps in viscosity profiles (generally less sensitive than using chemical compositional data) and needs to be typically better than about ±20% of the true value to make decisions regarding cold versus thermal production in very heavy oils or oil sand bitumen reservoirs. Typical laboratory viscosity determinations have errors in the order of 1-5% and this level of accuracy may be attainable at the well site by recovering and measuring a more or less pure bitumen sample in near real time at the surface or downhole. Current in situ oil viscosity assessment technology such as those using downhole NMR properties provide viscosity estimates that may not meet these criteria, especially for heavy and extra heavy oils and bitumen.

The determination and incorporation of sufficiently precise and accurate absolute viscosity value data for heavy oil and bitumen and spatial variations of viscosity at a vertical resolution of about one sample per 1-5 m of reservoir section into production planning and recovery process design and operation may be achieved in real time resulting in a significant improvement in the operational efficiency and enhancement of the overall level of productivity.

Chemical and fluid property analysis of reservoir fluids extracted from the reservoir under in situ reservoir conditions may be advantageous to reservoir engineers and geoscientists. This is especially important in heavy oil fields where the petroleum often will not flow at native reservoir conditions. Advances in the ability to sample and characterize reservoir fluids that flow under in situ conditions have been made in the last decade with dynamic well testing systems coupled to optical spectrometers leading the way.

However, current tools may not be able provide the molecular information necessary for many geochemical applications such as detection of barriers or baffles within reservoirs that partially or completely attenuate fluid flow during oil production or, in situations where oil cannot flow into the tool, as is common in bitumen and heavy oil reservoirs, they do not operate at all.

The present disclosure describes a method for rapidly and inexpensively recovering reservoir fluids from heavy oil and bitumen reservoirs for geochemical or fluid property analysis of reservoir fluids (e.g., oils, waters, gases) in situ and describes some technical advances that will enable high resolution molecular geochemical applications and high resolution fluid property and fluid saturation assessments, as well as, replacing expensive production testing procedures with rapid core sample based tests of such data to be performed in situ on a routine basis.

The method describes an in situ device for cleaning a borehole wall and drilling mud contaminated reservoir material to enable a sampling probe or corer device to recover reservoir fluids or a whole reservoir sample recovery system to be inserted into the formation. The present disclosure further provides for recovery of reservoir fluids via solvent extraction and characterization of the fluids using a sensor system to recover chemical information that can be used to derive, through correlations with a baseline sample set, an in situ viscosity, API gravity, TAN or any other fluid property measurement. The method also permits determination of the oil and water saturations of the rock.

Determination of the viscosity of oil and bitumen has typically been carried out in the laboratory on more or less pure samples of oil or bitumen using a viscosimeter, viscometer or rheometer. For conventional black oils and condensate oils recovered during production or using a typical drill stem or other fluid testing/recovery method, the loss of small amounts of volatile components during sampling, transportation, storage and analysis is not desirable but may not have a large impact on the final measured value of the property. However for heavy oil and bitumen samples, the loss of even small amounts of volatile components (gases or volatile compounds that act as effective solvents) may cause large changes in the measured viscosity. Similarly, the contamination of a heavy oil or bitumen sample by small amounts of material that can act as a solvent, such as low molecular weight organic substances incorporated into drilling mud or fracturing fluids, can cause very significant reductions in the measured viscosity of the heavy oil or bitumen sample.

The method described herein may be used to recover properties for a heavy oil by using the properties measured on a solvent extract of the whole reservoir sample (matrix minerals, formation water, drilling fluid plus oil/bitumen).

Pending U.S. application Ser. No. 12/673,768, incorporated by reference as if fully set forth herein, describes a method for obtaining a physical viscosity measurement (using a viscometer or rheometer) of a heavy oil or bitumen sample that has been extracted or diluted or otherwise handled with a solvent and therefore contaminated with that solvent. This is accomplished by partially removing solvent from a mixture of carefully chosen solvents to ensure that the volatile components in the sample are not inadvertently removed during the partial solvent removal and then carrying out a series of viscosity determinations on the solvent plus oil mixtures. These viscosity determinations are coupled with a determination of the amount of residual solvent content at each step, followed by an extrapolation to a zero solvent content viscosity estimate. This approach could be used in situ if an appropriate sampling system and viscometer were employed. The method can also be extended by adding, rather than removing different quantities of solvent, such that viscosities measured on oil solutions in solvents at different concentrations can be used to derive an accurate viscosity for a non diluted oil sample.

The present disclosure is directed to rapid, accurate in situ (within the drill hole) determination of the live oil (solution gas charged) viscosity, or other bulk property of the oil or bitumen in reservoirs, geochemical analysis of key components of the oil and oil and water saturation using a reservoir sampling system and a sensor mounted into an appropriate logging tool. The in situ method provides the advantage of providing the freshest possible sample from which the minimum amount of volatile components has been lost because the reservoir material has never been depressurized. The present method may provide a viscosity determination on the freshest possible sample and thus will be close to the viscosity of "live oil" that is, as it was present in the reservoir prior to drilling. This minimizes the extrapolation from measured viscosity to true, live oil viscosity and thus reduces the error of the live oil viscosity estimate and thus improves the accuracy of the engineering evaluation of the reservoir.

Oil viscosity measurement at surface typically involves recovery of a more or less pure oil or bitumen phase from recovered reservoir rock samples using core sample compaction or high speed centrifugation, or displacement of the oil with an immiscible viscous fluid (mechanical recovery techniques) to recover a solvent free oil, followed by analysis of the oil viscosity with a viscosimeter, viscometer or rheometer. This process cannot typically be done in situ within a drill hole and thus volatile components of the oil or bitumen are typically lost during the recovery, transport and storage of the samples. Insertion of the Plunger or other mechanical device into a downhole tool with an in situ sample cleaner and core delivery and removal system plus an in situ viscometer could remedy this problem.

More sensibly however, various chemical proxy methods of determining oil viscosity or other sensitive oil property such as oil pour point, API gravity or total acid number (TAN) can be applied in situ using appropriate sensors mounted into downhole logging or sampling tools. The same proxy methods may also be applied to provide real time viscosity determinations at the well site on cuttings or core samples as these materials are brought to the surface during the drilling operation or subsequently, in a laboratory. A proxy method does not determine viscosity or other property directly but instead uses a baseline calibration suite of oils and chemical analyses to establish a correlation function which can then be applied to a chemical analysis data set from a target sample to derive an accurate fluid property such as API or viscosity. As the method is chemically based using a correlation, with an appropriate chemical sensing technology, using for example mass spectrometry or optical spectroscopy, target chemical features relating to the fluid property correlation can be extracted even from contaminated mixtures of fluids, an advantage in a downhole environment. Such a method, as described here, implemented in situ would permit easy assessment of oil viscosity, API gravity, pour point or acidity (TAN) or other property The method uses the determination of chemical properties of the bitumen that are then used as a proxy to determine the viscosity or other property of the oil or bitumen sample. These chemical properties may include the infrared spectrum and/or the mass distribution of molecular or fragment ions of the organic constituents in a sample or the responses of electronic nose type sensors to the cocktail of components within a crude oil sample.

The chemical and/or physical property measurements are made using one or more sensors specific to the presence, absence or relative quantity of numerous chemical components in the sample and/or the extent of physical properties for which a suitable proxy calibration has been completed. Highly specific sensors will provide analysis results in about one minute or less. The sensors are sufficiently robust to be deployed into the drill hole within a logging tool and/or operated in the field at the well site.

The sensor data may be tuned to be specific to the oil or bitumen phase by examining sensor response contributed by only the target analyte and thus the method is insensitive to solvents or drilling fluid additives and thus sample handling may be facilitated by the use of solvent either in situ or at the well site. The sensors can also measure the absolute quantities of oil and or water in a recovered fluid or solvent extract sample allowing fluid saturations to be determined.

The chemical and/or physical property measurements can be made from either the whole rock sample (e.g., drill hole wall for in situ measurements or cuttings/core samples for the well site or laboratory measurements or on outcrop samples in the field) or on a bitumen sample that has been suitably separated from the solid rock matrix plus formation water either in situ or at the surface or recovered as a test sample using an appropriate testing device or method. That is, the method can obtain data from solid or fluid samples. Crucially, the measurements may be made on a solvent solution of the bitumen. While traditionally, solvent containing oils are not considered appropriate for determination of viscosity, both chemical proxy approaches, and direct measurement of solvent oil viscosity mixtures with varying solvent content can be used to obtain reliable oil viscosity data. Thus solvent recovery of oil (and water) from reservoirs is a novel approach to obtain in situ fluid data and solves the fundamental problem of using flow based sampling tools in heavy oil and bitumen reservoirs where fluids will not flow. Both chemical (proxy based) correlation methods and direct solvent mixture based in situ viscosity measurement methods can then be used to derive reliable viscosity measurements. The device described here can thus produce a fluid sample of live oil and solvent for fluid characterization from reservoirs where no natural flow of fluids is possible.

Systems, devices, and methods of the present disclosure can be implemented to exploit knowledge of both the absolute viscosity values and spatial variations in the viscosity to realize one or more of the following advantages. By using the process described, viscosity of oil can be rapidly determined for samples of viscosity to at least $30 \times 10^6$ cP at a temperature of 20° C. Viscosity can be accurately measured in situ in the drill hole on small fluid samples of much less than 1 g of recovered oil and water in solvent. The viscosity can be measured on high oil saturation reservoirs or on low oil saturation reservoir samples of less than 8 wt % oil where oil flow is naturally limited. The viscosity can also be measured for samples that have been damaged during drilling caused by the contamination of oils with volatile compounds including oils introduced into the drill hole, such as in the drilling mud. The absolute viscosity can be made rapidly at a large number of vertical (in a vertical well) or horizontal (in a horizontal well) sampling points (in situ) or a large number of recovered samples (well site or laboratory on surface recovered rock material, either core or cuttings)) thus providing sufficient spatial resolution of the data to make reliable and credible viscosity profiles required in heavy oil and bitumen reservoirs where viscosity changes very rapidly as a function of depth. The absolute oil viscosity values can be measured in real time allowing for immediate assessment as to the suitability of a reservoir to be developed through cold production or enhanced production strategies or to ascertain that economic production is not possible at all.

Dead oil viscosity of oil in a petroleum reservoir, especially oil sands and bituminous carbonates, can be determined using physical and/or geochemical procedures either at the well site by analysis of reservoir core at the surface with oil extraction and use of a viscometer or rheometer. Geochemical estimates of physical properties of a reservoir fluid from a tiny amount of petroleum is always feasible too using chemical proxy approaches. Measurement of oil viscosity from solvent extracted oils is also possible using measurements at several solvent concentrations. Such methods can produce a baseline study of oil viscosity in an area.

During delineation well drilling, heavy oil or oil sand core samples are routinely taken for reserve assessment and production process design purposes. A small amount (e.g., 250 g) of the fresh core material can be collected at the well site from both ends of the core barrel or from the ends of barrel cuts, or from within the core itself and can be mechanically extracted to recover an oil or bitumen sample. Five to 10 g of more or less pure bitumen can be recovered in most cases, which can be analyzed immediately for viscosity (and density/API gravity) at different temperatures. This whole procedure can be completed within 90 minutes or less. Of course these same core samples are always good enough for geochemical analysis to estimate viscosity.

Oil or bitumen recovery by mechanical compaction may not be successful on every core sample, especially for those with low bitumen content (e.g., <5 wt %) and/or oil sand cores containing very high viscosity oil or in highly lithified, non-compactable carbonate cores. For these types of refractory core samples, ProxVisc™ (e.g., viscosity determination on a solvent recovered oil using a chemical proxy) may be a better choice to estimate the dead oil viscosity as it will work for very small samples even if they are contaminated by drilling or fracturing fluids. Gas chromatography-mass spectrometry (GC-MS) analysis is carried out on the solvent extracts of bitumen or heavy oil from the refractory core samples to reveal the quantitative composition of organic molecular markers containing source, maturation and post-charging alteration (e.g., biodegradation) information. By comparing the geochemical composition of the refractory cores with those of the produced oils and/or cores on which viscosity measurement has been performed in addition to GC-MS analysis, the viscosity of the refractory sample fluid can then be calculated.

ProxVisc™ is a method to effectively estimate oil viscosity for samples that yield no, or insufficient, or insufficiently pure mechanically extractable oil or indeed for any oil recovered by any means contaminated or otherwise. ProxVisc™ utilizes molecular geochemistry to predict bitumen viscosity and/or API gravity from the quantitative analysis of concentrations of various hydrocarbon and non-hydrocarbon compounds, that is, their chemical fingerprints. For optimal use a set of chemical measurements and physical property data for a suite of calibration oils that are related to the test samples are used to provide an appropriate relationship between viscosity and detailed chemical composition.

Sample types include any mechanically or solvent extracted oil samples, small, low porosity, or low oil saturation reservoir samples; highly viscous oils, outcrop reservoir rock samples, or cuttings; drilling mud or otherwise contaminated samples. Suitable samples include old, thawed core and cutting samples (1 g of core or cuttings, or 200 mg of bitumen) or solvent extracts such as the bitumen extracted using toluene during a Dean Stark analysis or bitumen recovered by mechanical means (e.g., a plunger or centrifuge or other means) but in quantities too small to measure by conventional viscometry methods. The benefits of being able to analyze small samples (<3 g of rock) allows viscosity estimates from publicly available small archive samples; viscosity from cuttings yielding small amounts of oil; profiling oil viscosity in carbonate reservoirs where mechanical oil extraction is not possible and of course in situ analysis is also possible.

Figure 5A:
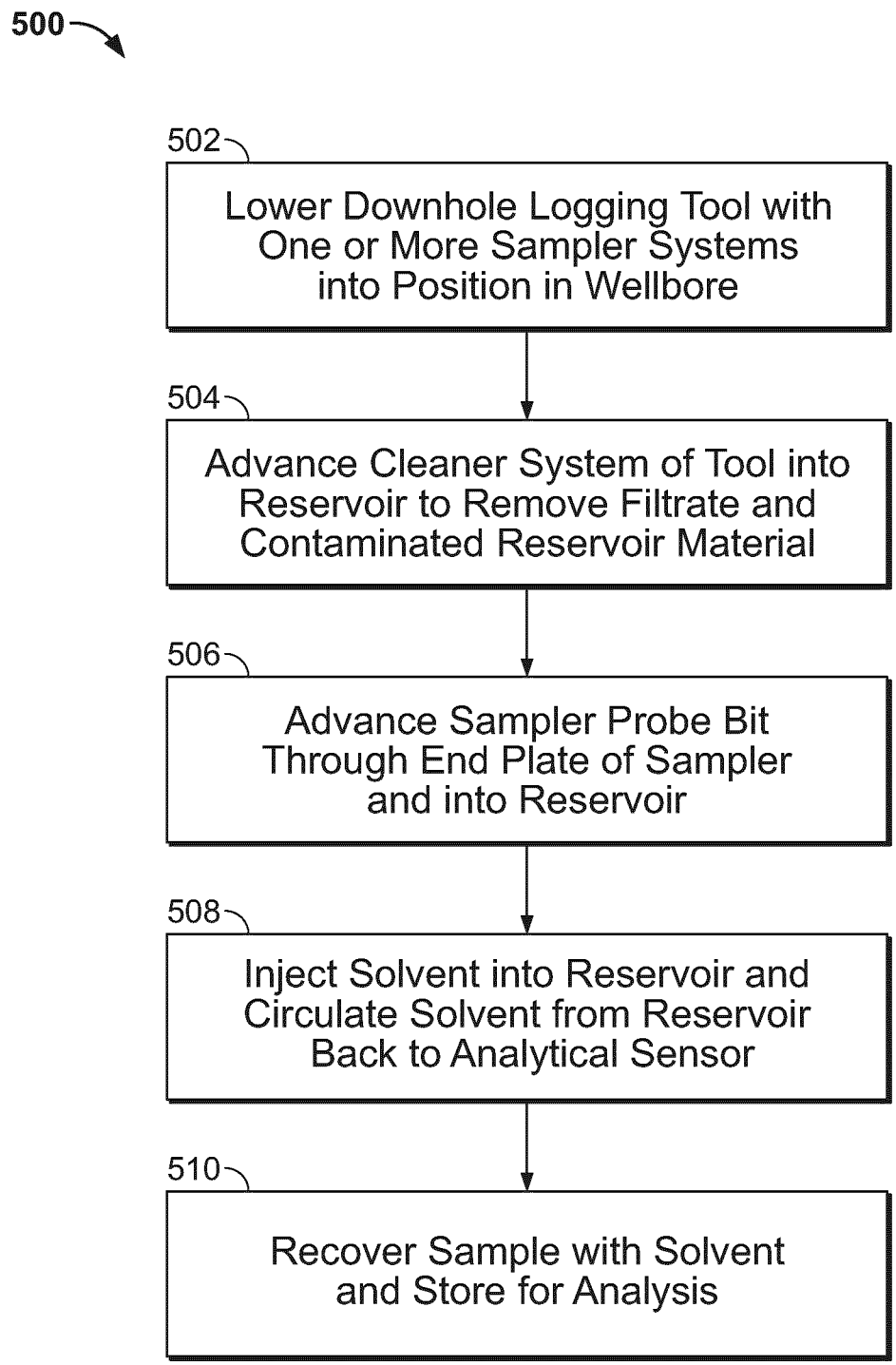
FIG. 5A illustrates an example operation of the example sampling device shown in FIGS. 3A-3B and 4.
Figure 5B:
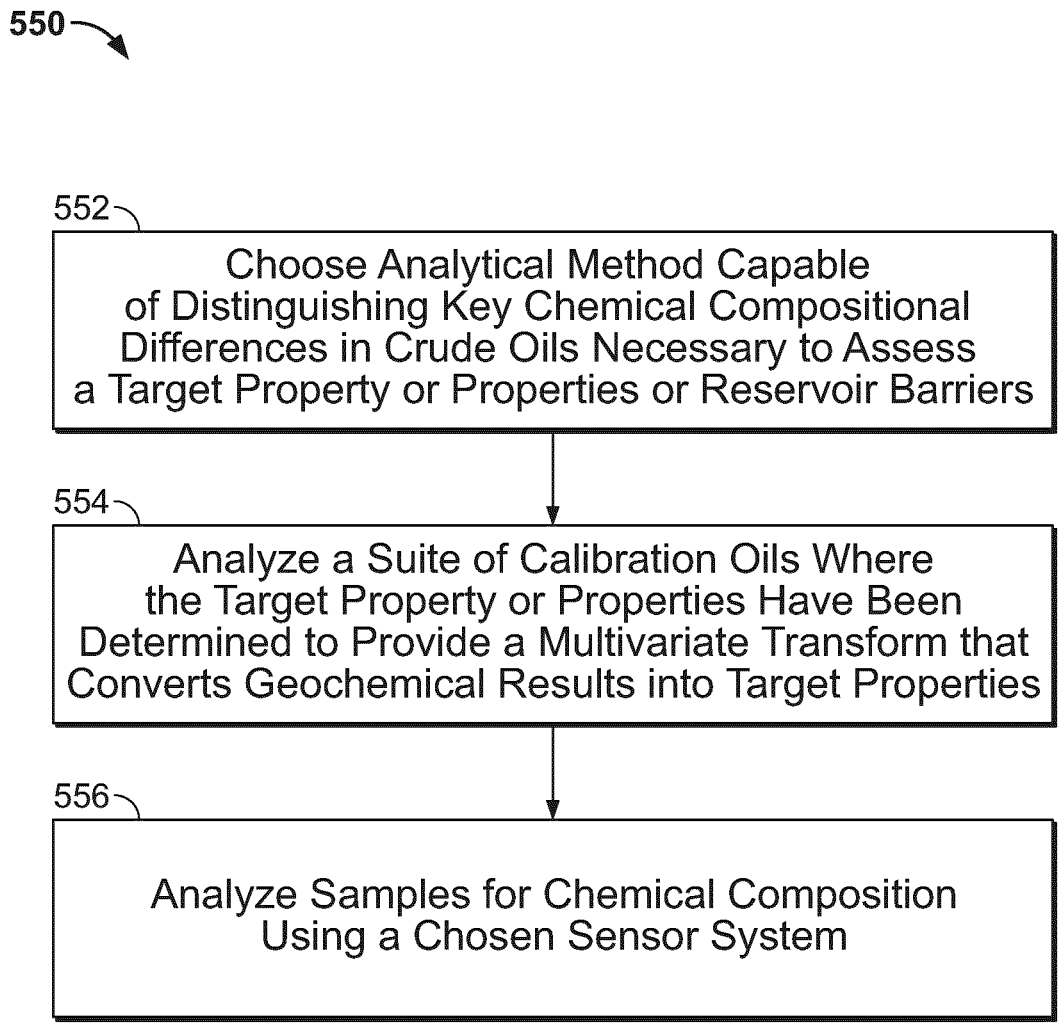
FIG. 5B illustrates an example operation for an oil property by chemical analysis and chemometrics.

FIG. 5B illustrates a method 550 for assessing viscosity or other oil property (e.g., API, gas oil ratio (GOR), formation volume factor or other PVT property, TAN, pour point, or otherwise) by chemical analysis and chemometrics—ex situ or in situ. In step 552, an analytical method capable of distinguishing the key chemical compositional differences in crude oils necessary to assess a target oil property or properties (e.g., viscosity) or reservoir barriers. The assessment may be done, for example by chemical proxy. This may involve assessing a chemical compound type (e.g., concentrations or distributions of specific hydrocarbons and/or non-hydrocarbons with heteroatomic functional groups); molecular weight differences that can indicate whether the oil is dominated by light end material or heavy end material and identify and track key geochemical processes that control oil viscosity such as petroleum biodegradation or oil source facies or maturity.

In step 554, a suite of calibration oils from the study area are analyzed where the target property (e.g., viscosity data) has been determined by classical means to provide a multivariate dataset and transform that converts geochemical results into viscosities using multivariate statistics and/or neural network analysis and correlation. In the analysis cycle, oils extracted from target core or cuttings samples are analyzed geochemically and the result is converted via the multivariate transform function to a viscosity estimate. Target property measurements would be made under appropriate conditions so if dead oil viscosity is required, dead oil viscosity measurements would be used as calibration data, if live oil viscosity measurements are required, live oil viscosity target data would be used. If other properties were to be assessed (e.g., TAN) they would form part of the calibration dataset.

In step 556, samples are analyzed for chemical composition using the chosen sensor system. Sensor types evaluated include gas chromatography or GC-MS based systems or ion mobility MS systems or optical spectroscopy systems such as Fourier transform infrared spectroscopy (FTIR) systems and electronic nose systems.

Examples of specific sensors could include, but are not limited to, an infrared sensor and an electronic nose. Fourier transform infrared spectroscopy provides data for a wide range of wavelengths with short analytical times and many systems are available including small low power, portable systems that can analyze solutions or whole oil based samples via transparent windows. Organic mass spectrometry with a wide molecular mass range up to ~1500 Daltons may be accomplished by using an ion mobility mass spectrometer operating in air or a gas phase, at or near atmospheric pressure and could be coupled to the device. Additional sensor devices could be based on optical activity, Raman spectroscopy, laser induced fluorescence spectroscopy, laser absorption spectroscopy, resonance ionization spectroscopy or modification of the electrical properties of suites of different electrically conducting polymers or carbons by adsorption or absorption of proxy components from the oils (electronic noses).

Infrared sensors are particularly useful in this application. In the case of an infrared sensor, the matrix of properties of the oil or bitumen would be the effective absorbance (or transmission) of the oil solution in solvent at various far or near infrared wavelengths. In the case of the mass spectrometer, the oil or bitumen properties would be the relative peak heights at various molecular weights. In the case of the electronic nose the data spectrum would consist of a set of responses from each sensor element, each element responding to a suite of specific component types. Sensor elements may be chosen to be sensitive to specific oil components that are known proxies for viscosity. These would include, for example, (1) Light hydrocarbons $C_1$-$C_5$; Intermediate hydrocarbons $C_6$-$C_{11}$; (3) $C_{12}$-$C_{40}$ hydrocarbons; (4) Specific indicators of biodegradation level such as the abundances of resistant hetero-compounds such as asphaltenes, thioaromatic compounds, etc.; and (5) Specific alkanes and aromatic hydrocarbons including specific alkylaromatic compounds.

In addition sensors capable of quantitatively detecting water and oil together in a mixture are desired and FTIR, MS and electronic nose systems are capable of this feature.

Chemical correlations with measured fluid properties using multivariate methods, e.g., partial least squares and neural networks have been applied to complex systems involving oils, coal and other substances by using geochemical components to predict key parameters for many applications. These methods can be applied quickly at low cost using limited measured data and tiny oil samples for the prediction sample set. To ensure calibration samples span the full compositional range of the prediction set, hierarchical cluster analysis (HCA) and/or principal component analysis (PCA) are commonly applied to define the most characteristic variables. The viscosity of an oil or bitumen sample is then determined from the matrix of physical and/or chemical properties by using a multivariate statistical analysis using partial or classical least squares analysis, principal components analysis, alternating least squares analysis, multivariate curve resolution, adaptive neural network analysis, or genetic algorithm or support vector machine non-linear correlation methods, through either a universal calibration composition-fluid property dataset for fluids in a region or via a calibration specific to a local oil or bitumen occurrence. The application of a large number of parameters measured simultaneously permits the deconvolution of the data specific to the property of interest, in this case viscosity. While fluid properties can be assessed quantitative geochemical compositions of components can also be determined by the same process and these compositional profiles down through an oil column can be used to assess reservoir compartmentalization or can be used to provide a baseline of oil compositional variations to serves as a production allocation baseline study. Thus, the concentrations of aromatic hydrocarbons in crude oils using FTIR data and multivariate correlations may be determined.

The proxy method of viscosity measurement, using a multivariate statistical approach also provides for an estimate of the error of the calculated oil property value allowing for a real time determination of risk factors, especially when viscosity values are close to critical physical and/or economic limits and crucial decisions must be made.

For GC based analytical systems, quantitation of the contents or distributions of up to several hundred chemical compounds using an array of internal standards provides for the calibration of samples in both a relative and absolute concentration context. For the most accurate and precise data a heavy oil or bitumen sample is first chromatographically cleaned by passing the oil through a high polarity adsorbent such as a fluorinated silicone or clay which removes the most polar crude oil fractions and allows subsequent chromatographic separation of clean consistent hydrocarbon fractions very suitable for very accurate quantitative GC-MS analysis. Similar absolute weights of sample (~40 mg) and volumes of solvent (~1 ml), an automated injection system and retention time locking during GC-MS provide highly reproducible, quantitative results. By analyzing a standard suite of aromatic and saturated hydrocarbons and non-hydrocarbons using gas chromatography-mass spectrometry (GC-MS) and correlating the results against a calibrated viscosity or API gravity data set, the level of biodegradation and oil quality can be assessed for samples for which properties cannot be determined directly. That is, standard samples with known physical properties are used to develop geochemical proxies for those properties. With appropriate calibration data sets, the viscosities obtained from the correlation technique typically fall within 10% of conventionally measured viscosities.

Figure 7:
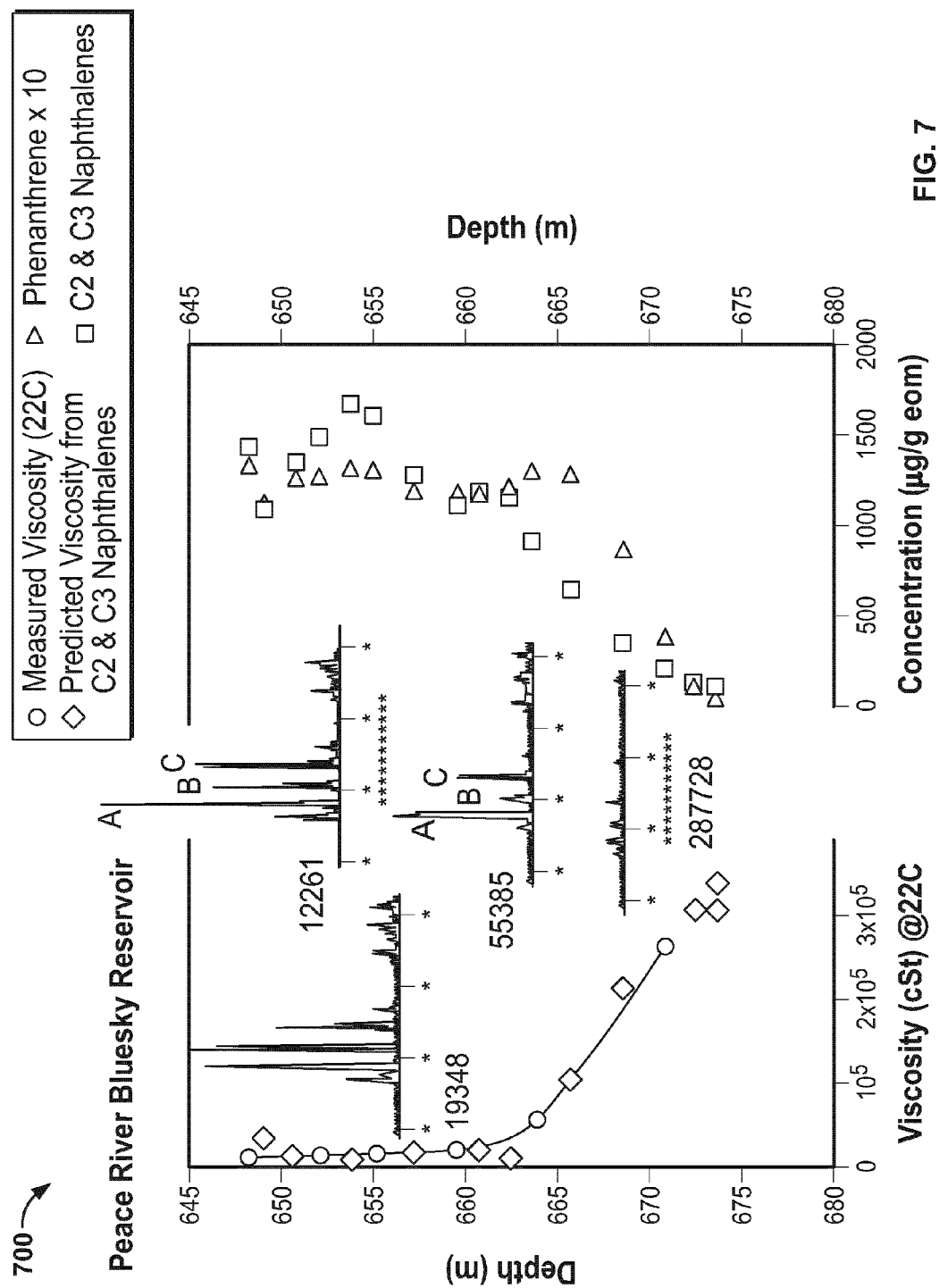
FIG. 7 illustrates dead oil viscosity and chemical composition for bitumens in a Bluesky Formation reservoir in Peace River.

Even without local calibration data, viscosity estimates are better than an order of magnitude in accuracy. FIG. 7 (modified after Larter, S., Adams, J., Gates, I. D., Bennett, B. and Huang, H., "The origin, prediction and impact of oil viscosity heterogeneity on the production characteristics of tar sand and heavy oil reservoirs," Journal of Canadian Petroleum Technology 47, 2008, pp 52-61) shows application of the basic approach in an oil sands bitumen reservoir and, more specifically, dead oil viscosity and chemical composition for bitumens in a Bluesky Formation reservoir in the Peace River oil sands, where directly measured oil viscosity and chemically assessed oil viscosity are compared and show good agreement. In this case surface analysis of solvent extracted reservoir core provided the data for analysis. It can be seen that geochemical proxy data and classically measured viscosity data are very comparable.

While large GC-MS systems are not easily configured downhole in a typical logging tool environment, small portable direct inlet ion mobility mass spectrometers, without GC separation of mixtures are routinely used in security applications and do have applicability to downhole fluid characterization activities coupled with samplers described here.

Alternatively to GC-MS or MS techniques, a spectroscopic chemical sensor highly sensitive to various individual compounds and classes of organic compounds, such as an FTIR spectrometer may be used to rapidly provide a sufficiently detailed chemical fingerprint of the samples with little or no sample preparation. Advantages of using this type of sensor include small size, low power requirements, no external gas or vacuum supply needs, plus operational robustness allowing it to be applied in a well site operation or downhole. Such sensors can operate with gas phase, liquid phase or solid phase samples.

Figure 8:
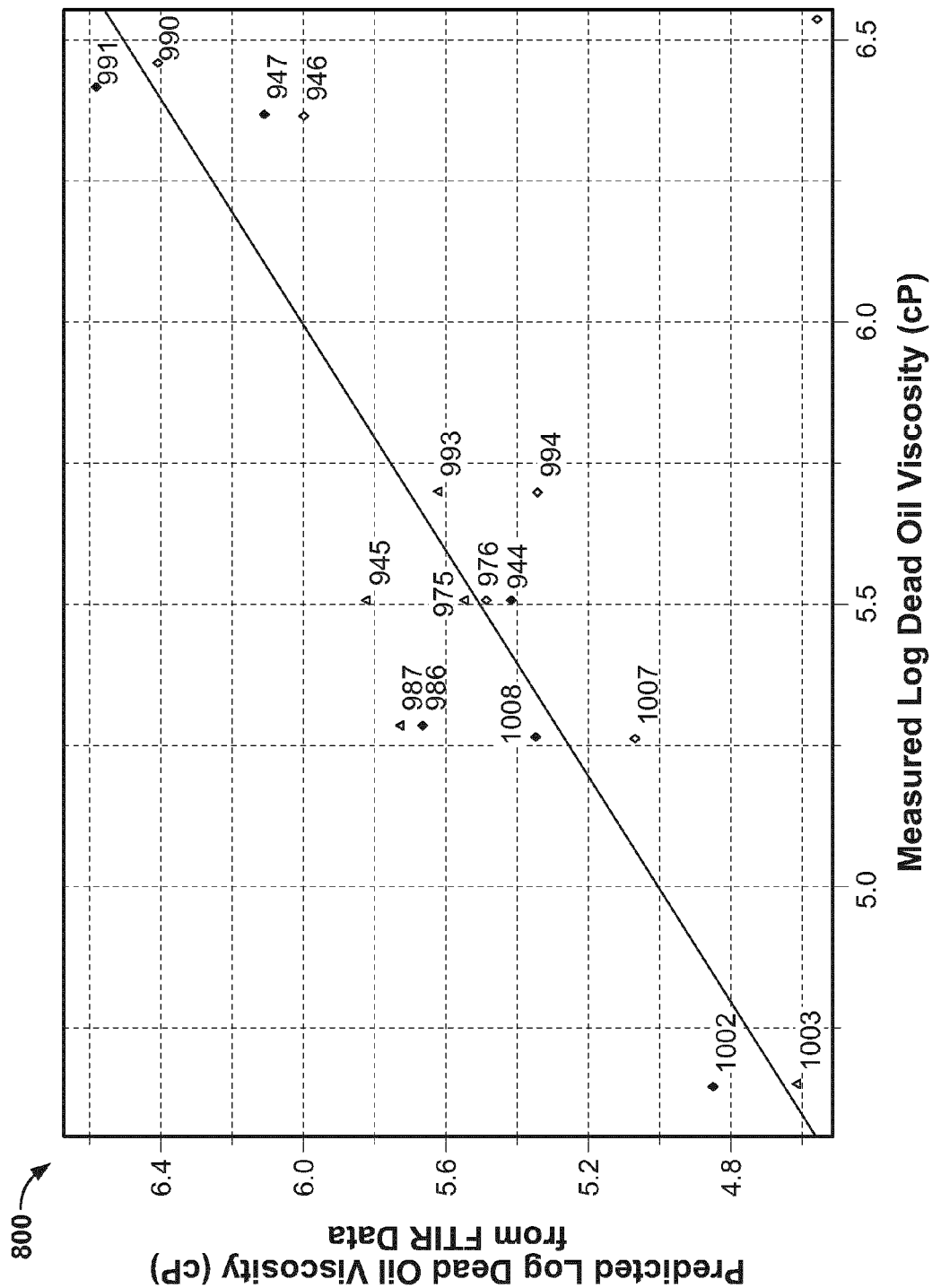
FIG. 8 illustrates measured (X axis-using a viscometer) and predicted (Y axis-using Fourier transform infrared spectroscopy (FTIR) data) log oil viscosity for a series of Alberta bitumens in the presence of water and $CO_2$ contaminants using a small portable FTIR spectrometer sniffing oil vapors in a simple vapor sampling system.

Referring to FIG. 8, the application of FTIR spectroscopy to the measurement of oil viscosity is illustrated in samples with other species present and FTIR is also effective for the assessment of the effectiveness of the processing performance of oil sands mined ore when processed using a warm water treatment system or other bitumen separation process. Thus FTIR, which can resolve the surfactant property controlling functional group distributions of non-hydrocarbon molecules, as well as assess carbon-carbon and carbon-hydrogen bonding environments and respond to changes in molecular weight distributions, is an ideal means of making a proxy chemical measurement for prediction of a wide range of physical and chemical properties of heavy oil, bitumen or conventional petroleum (including API gravity, viscosity, TAN, pour point, and surface processing behavior in a mine separation or refining process). FTIR or FTNIR spectroscopy can also resolve water presence in the presence of hydrocarbons and can also determine the absolute quantities of oil and water present in a mixture of oil, water and solvent. Thus determination of water contents of a sample using, for example, absorption at wave numbers of 4000-3400 $cm^{-1}$ and 2000-1300 $cm^{-1}$ can be made while oil abundances and oil compositions can be simultaneously assessed using absorption at 2800-3200 $cm^{-1}$ and at 1000-1200 $cm^{-1}$.

Carbon dioxide contents of fluids can be assessed using absorption at 2200-2400 $cm^{-1}$ thus the method can be used to assess $CO_2$ contents of reservoir fluids and thus has application to carbon storage studies. Thus FTIR spectroscopy can be used to assess oil and water saturations by analysis of water and oil contents in a solvent extract of a rock and also assess the physical properties of the petroleum in a solvent mixture. Using multivariate analysis approaches, deconvolution of overlapping absorption bands from multiple components across the whole spectrum can be achieved. Other spectroscopic methods including visible light spectroscopy and UV-visible light spectroscopy can also be used.

FTIR spectroscopy can be used, together with chemometric techniques such as principle components analysis, partial least squares regression and multivariate curve resolution to infer the absolute concentrations of specific chemical markers in a mixture from analysis of FTIR spectra. Thus, for example the absolute concentrations of alkylphenanthrenes, alkylnaphthalenes or other molecular species that have been measured in a calibration suite of oils by GC-MS methods can be determined on target oils using FTIR spectroscopy and chemometric methods. Thus the approach can produce component concentration or other logs able to detect reservoir compartments (e.g., as in FIG. 6).

The electronic nose approach uses a set of electronic sensors whose electrical properties react to target analytes and whose array of responses can be calibrated to the presence or concentrations of target analyte components in a mixture. Using established chemometric techniques as described above, the electronic nose approaches can provide similar predictive capability to the GC-MS and FTIR based systems discussed above. Most electronic noses use sensor arrays that react to volatile compounds or compounds of different polarity on contact, the adsorption of volatile compounds on the sensor surface causing a change in the sensor. The most commonly used sensors include metal oxide semiconductor (MOSFET) devices, electrically conducting polymers, or quartz crystal microbalances. These electronic sensor arrays have established environmental and chemical security monitoring roles and are viable low power sensor systems suitable for assessing chemical composition for predicting oil and water contents and properties in samples, solvent solutions, or directly extracted from reservoirs.

For an oil viscosity suite the key chemical signals (compound concentration variations or variation of key spectral wavelengths, or wavenumbers within a calibration oil suite) that are optimal for tracking and predicting oil viscosity, or any other parameter, can be selected using techniques such as principal components analysis or by choosing chemical signals that show significant correlations with viscosity (or other parameter) and large variances within a calibration sample set. Several types of chemical spectral data can be used for the technique including gas chromatographic data; mass spectral data; optical spectroscopy at infrared, UV or visible light wavelengths. The key is to have reproducible quantitative data that relates spectral response as a function of retention time (GC or GC-MS techniques) or wavelength or wave number (FTIR or other spectroscopies) to target properties of the reservoir samples under study.

In some embodiments (e.g., method 500), disclosed in the present application, several steps may be implemented to obtain a live oil viscosity or other fluid property in situ. For example, a first step may be to clean the borehole wall of mud to avoid or minimize contamination or otherwise avoid sampling drilling mud filtrate when recovering petroleum sample. The second step may be to recover a clean, drilling fluid free mixed oil and water fluid sample at formation temperature and pressure (FTP). If this cannot be achieved a solvent recovered oil samples can also be assessed even if contaminated. The third step may be to measure the fluid viscosity directly or indirectly using ProxVisc™ approaches at FTP. The fourth step may be to ideally retain a separate pressurized fluid sample for transport and analysis at the surface.

An array of physical and/or chemical properties of a bitumen or heavy oil is measured using one or more sensor devices that are specific to the oil or bitumen phase. The use of one or more oil-specific or bitumen-specific sensors allows the measurements to be made on a "raw" sample of reservoir rock including the mineral matrix and formation water. The sensor also allows the determination of the physical and/or chemical properties in the presence of an organic or other solvent with properties that do not interfere with the sample/sensor combination. Examples of solvents include, but are not limited to, toluene, dichloromethane (DCM), chloroform, carbon tetrachloride or carbon disulfide that have distinctive spectrometric properties different from those of crude oils.

When liquid petroleum and associated solution gases are to be sampled a polar, spectroscopically and chemically distinct hydrophobic solvent such as dichloromethane, chloroform or carbon tetrachloride can be used. Isotopically labeled solvents with hydrogen replaced by deuterium can be advantageous as well.

When water samples are to be recovered for quantitation a hydrophilic polar solvent such as anhydrous methanol or acetone or other hydrophilic organic species can be used.

When both water and petroleum is to be extracted mixtures of a hydrophobic and hydrophilic solvent, solvent mixture such as dichloromethane and methanol in appropriate quantities can be used. A typical mixture might be dichloromethane 90% and methanol 10%, or 93% dichloromethane and methanol 7%.

When acidic fluids such as $CO_2$ or $H_2S$ in high concentration are to be sampled sodium hydroxide solution or other aqueous alkaline solutions can be used.

The modified wall cleaning sampler described above may perform one or more operations. For example, the device scrapes off the surface mud/filtrate and places a sealed container on the cleaned reservoir surface. A sampler probe is then drilled through the cleaner system into the reservoir and a small volume of a spectroscopically distinct polar solvent (dichloromethane for example) is injected into the reservoir through the sampler bit or in one embodiment the needle is screwed into the formation. In another version a capillary carrying auger is screwed into the formation and the solvent injected.

After injection of solvent into the reservoir, a period of time allows the solvent to extract the reservoir oil with its solution gas or the reservoir water or both. The pump module then retrieves the solvent and oil which will have variable concentrations of oil depending on fluid access and mixing. Only small volumes of solvent (<<5 ml) are used to minimize the risk of solvent accessing the in well bore cavity or of contaminating the environment.

As the fluid is withdrawn into the device by the pump it passes through the sensor package (the description below implies an FTIR spectrometer but other sensor signals can be used as described above) whereby the solute concentration is assessed based on the relative proportions of a distinct absorption in the solution. Water is assessed using unique absorption bands or responses of water, while crude oil is assessed using sensor responses appropriate for hydrocarbons and non-hydrocarbons in crude oils. Measurement of the viscosity can be made using a commercial in line viscometer in series with or replacing the sensor package.

If direct viscosity determination is required and a viscometer is part of the sensor system, viscosity of the solvent free live oil can be made using mixing rules or a variety of simple procedures. For example, a cross plot of ln(viscosity) of the solvent mixture versus the ratio of a unique absorption or sensor signal of the oil to a unique absorption or sensor signal for the solvent, for several measurements of oil solutions at different oil and solvent concentrations, extrapolated to zero solvent content projects to a value for the live oil viscosity. If Vm is the mixture viscosity at one concentration of the solvent assessed spectroscopically and $Vm_2$ is the viscosity at double the solvent concentration then the true live oil viscosity is given by.

$$Voil = \frac{Vm^2}{Vm_2}$$

This is applicable even if the absolute concentration of solvent is not known and thus the device can simply add aliquots of solvent to the extracted oil solution and then measure viscosity using a viscosimeter, e.g., at analytical chemical sensor system 312, and thus this can be used to determine viscosity. This method is applicable to any oil systems light or heavy. Retaining the solvent/live oil mixture in a sealed container could allow for restoring the sample at pressure to the surface for detailed analysis.

Alternatively using a simple spectroscopic system such as an FTIR spectrometer to measure oil concentration in the recovered solvent and the ratio of oil concentrations in two such recovered solutions of oil obtained by multiple solvent circulations (ratio described as −n) then the actual viscosity for the oil can be assessed using the relationship for the oil viscosity of:

$$Voil = \exp\left(\frac{-\ln(Vm_2) + n - \ln(Vm)}{-1 + n}\right)$$

where Vm and $Vm_2$ are the viscosities of each solution.

Both MS and FTIR spectroscopic characterization of oils can predict oil viscosity using chemometric correlations. The same sensor data can also predict the concentrations of specific geochemical markers such as specific saturated hydrocarbons, aromatic hydrocarbons or biomarker compounds in oils. Using this data geochemical logs can be produced that can assess whether a reservoir is compartmentalized and separated into different compartments by barriers or baffles (partly sealing barriers by looking for compositional steps in oil composition profile.

While the instrument can be operated to obtain samples of reservoir fluids it can also sample drilling mud fluids in situ and if oil shows are present characterize these to describe the oil composition and fluid properties.

Coupling an in situ fluid recovery system based on a solvent extractor of oil and water allows several methods of in situ viscosity and chemical composition assessment. Several methods of viscosity assessment emerge.

ProxVisc™ can be used with existing sensor technology (IR, IM mass spec, electronic nose or other) providing a rapid multidimensional (<2 min) data matrix of many dozens of variables that can be converted to a viscosity, or other fluid property, assessment using multivariate statistical methods or neural networks or other non-linear pattern recognition and correlation approaches and an external calibration dataset obtained from fluids in the area or similar fluids elsewhere.

By using a suite of calibration oils of different viscosity for an oil type from a specific location, and by assessing the correlation coefficients and variance of the responses of the sensors at many instrument response points (e.g., different wavelengths for an optical spectrometer or mass to charge ratios for a mass spectrometer) the most characteristically variable parameters for distinguishing oil properties in a given suite of oils can be made.

The method provides an extension of technology that enables bitumen to be characterized in the presence of solvent at surface or in situ in the reservoir rock sample and it can be operated at the surface on any sample that is recovered (fresh conventional or sidewall core, cuttings, bitumen, pressurized core, pressurized sidewall core, production oil).

Figure 9A:
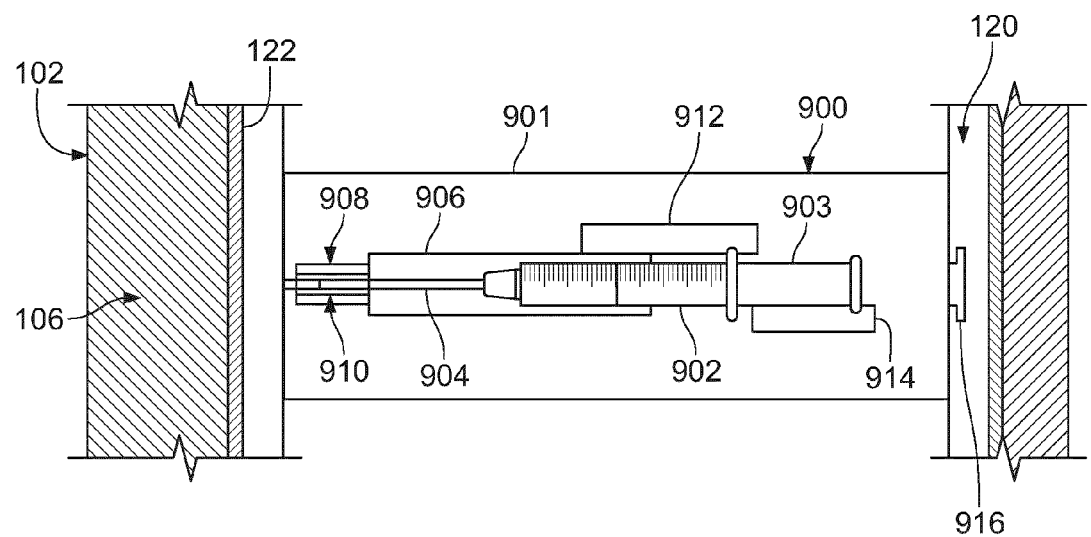
FIGS. 9A-9B illustrate another embodiment of a sampling device.
Figure 9B:
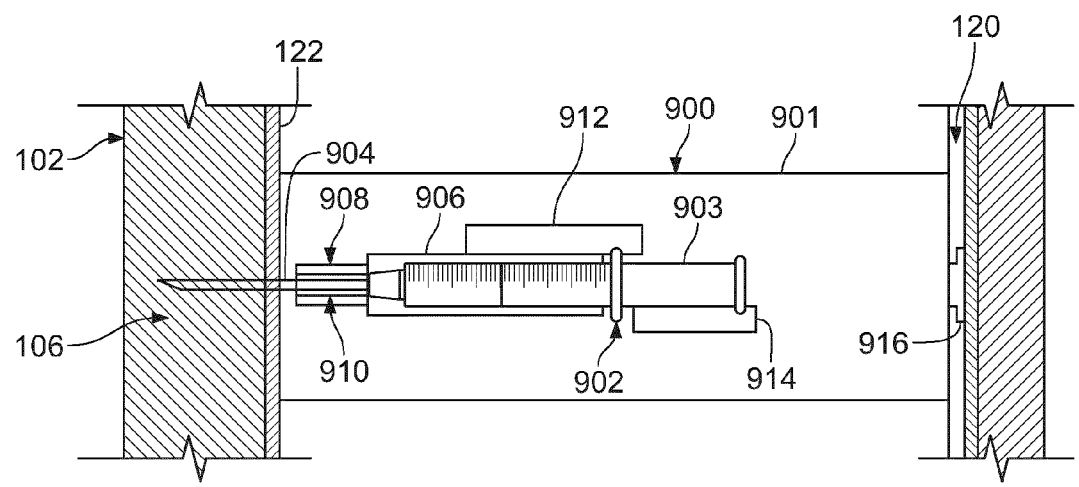

FIGS. 9A-9B illustrate another embodiment of a sampling device 900 in accordance with the present disclosure. This can be used with the wall cleaning systems described above, or without. In some embodiment, the sampling device 900 may be used in place of or in addition to the sampling device 114 illustrated in FIGS. 1 and 2A-2E. For example, at a high level, the sampling device 900 may be operated to recover a clean solvent extract of reservoir fluids, e.g., from the subterranean zone 106. For example, once taken, one or more fluids or other pieces may be extracted from the sample with an extraction device and analyzed by an analysis device as further described with reference to FIGS. 2A-2E, 3A-3B, 4, 5, and 10.

FIGS. 9A-9B illustrate views of the sampling device 900. With reference to these figures, the sampling device 900 includes a housing 901 that at least partially encloses a syringe 902 that includes a cannula 904 that is at least partially enclosed within a syringe carrier 906, and a cannula guide 908. The syringe 902 and/or syringe carrier 906 may be coupled to a syringe drive 912, e.g., a spring or threaded drive that may oscillate the syringe 902 and/or syringe carrier 906 between a retracted position and an extended position (e.g., based on receipt of a control signal).

The syringe 902 further includes a plunger 903 that is coupled to a plunger drive, e.g., a spring or threaded drive that may oscillate the plunger 903 between an unactuated position and an actuated position (e.g., based on receipt of a control signal). Further, as illustrated in FIGS. 9A-9B, a brace 916 may be coupled to the housing 901 and extend to contact the wellbore 102, e.g., during operation of the syringe 902 to maintain sampler position in the borehole.

In operation, FIG. 9A shows the sampling device 900 at a particular location within the wellbore 102 (e.g., downhole) and adjacent the subterranean zone 106 (or any other formation or reservoir to be sampled). As shown in FIG. 9A, the cannula 904 is enclosed within the cannula guide 908 and a tubing 910. The syringe 902 is in a retracted position. As illustrated the brace 916 may be extending (or extended) to contact the wellbore 102 and, for example, stabilize a position (e.g., vertical, radial) of the sampling device 900 in the borehole 120.

Turning to FIG. 9B, this figure illustrates the syringe 902 (and more specifically the cannula 904) extended by the syringe drive 912 from its retracted state so that the cannula 904 is in contact with the wellbore 102 and disposed into the zone 106. In some embodiments, the cannula 904 may have either a ball or a pointed end and with an armored tip may penetrate unconsolidated reservoirs such as are common in heavy oil and oil sands settings.

The cannula 904 may take one of several forms. For example, as a conventional cannula with one or more end openings, the cannula 904 may block with reservoir material during penetration of the reservoir formation. As a side-opening cannula with an access port, however, the cannula 904 may allow solvent or solutions to be added, or removed from, the reservoir formation via a side port. A side port cannula may help ameliorate the issue of port blockage with reservoir material.

In some implementations, solvent may be slowly forced into the zone 106 and then, after a soak period in some instances, solvent and oil mixture is withdrawn into the syringe 902. The syringe 902 is then withdrawn and the cannula 904 may be sealed, e.g., by a silicone liner or sheath 910, which adds security in avoiding contamination of the cannula 904 by drilling mud filter cake. The solution of oil can be then ported to a sensor device via a valve and tubing, or the sample recovered in the sealed syringe 902 to the surface 104.

In some implementations, penetration of the subterranean zone 106 can be aided by adding a vibration device (not shown) to the cannula 904. Hydrocarbon, polar or aqueous solvents can be used with the sampling device 900. Further, in some implementations, a solvent solution of recovered hydrocarbon fluids may be recovered to the surface for further analysis. Alternatively, a detector, e.g., an IR detector or PCB device, may be installed in the sampling device to analyze the recovered fluid in situ. For example, if such a sensor or detector was mounted at a bottom of the syringe 902 (e.g., nearest the cannula 904), then an analysis would represent the recovered solution, whereas if the sensor was mounted at a top of the syringe 902 opposite the bottom, then the analysis would be of the headspace in equilibrium with the solvent solution.

Figure 10:
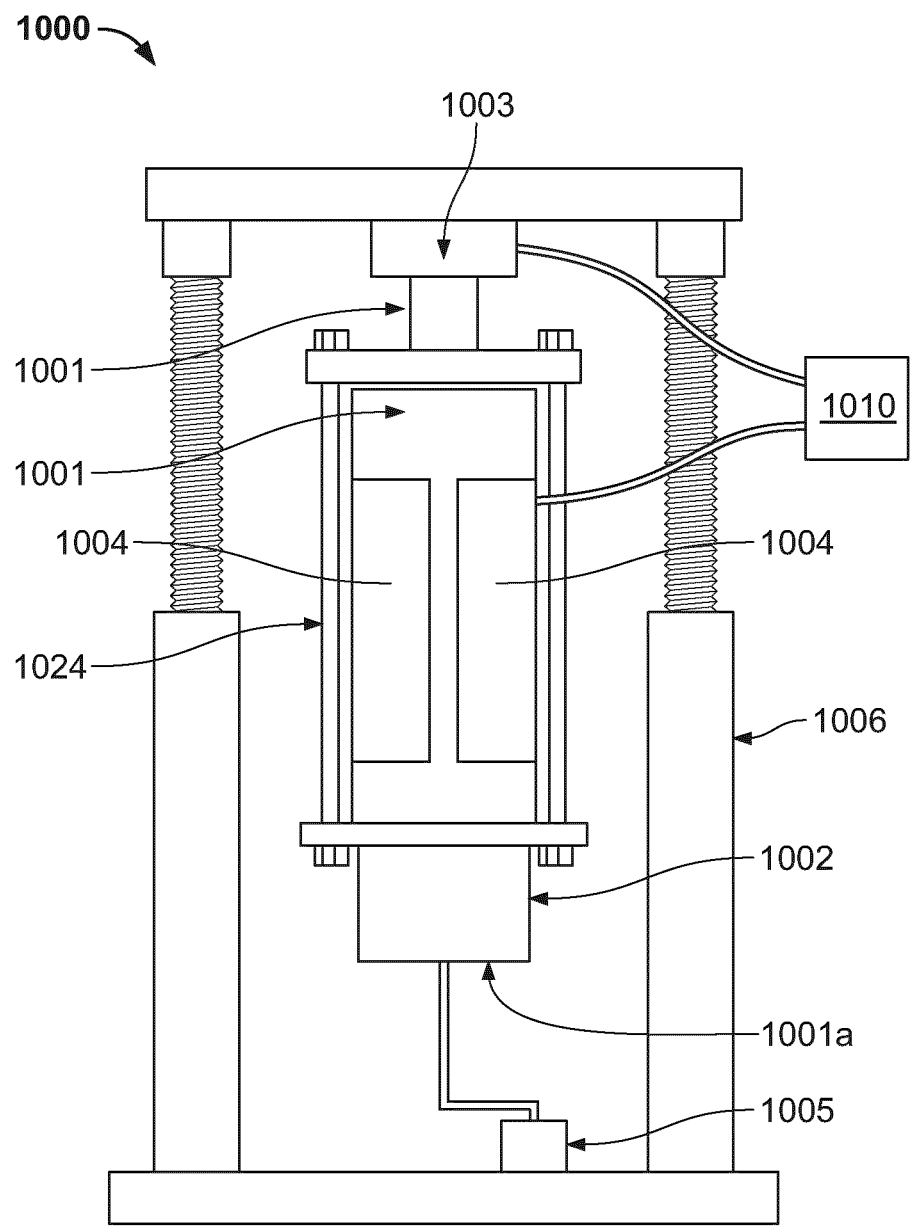
FIG. 10 illustrates an example embodiment of an extraction device.

FIG. 10 illustrates an example embodiment of an oil extraction device 1000 to remove oil from reservoir material. In some embodiments, the device 1000 may be used in addition to or in place of the extraction device 116 shown in FIG. 1. At a high level, the extraction device 1000 may extract heavy oil or bitumen in situ from a solid reservoir sample recovered by a sampling device, such as the sample 146 recovered by the sampling device 114. Pending U.S. application Ser. No. 12/526,608, incorporated by reference as if fully set forth herein, describes embodiments of an extraction device that recover more or less pure oil or bitumen with viscosity values up to about $30 \times 10^6$ cP (20° C.) by first squeezing out water and then oil and, by passing the oil through a filter system, a sediment and water free oil is obtained. This technology has been coupled with conventional fluid phase viscosity determination at the well site to obtain near real time viscosity values. As a sealed system the device recovers an oil sample with its solution gas intact and the gas content therefore depends on sampling conditions (e.g., surface or in situ). The device can be operated at the surface or in situ and can also be used to simulate a production process replacing a conventional production test.

As illustrated in FIG. 10, the extraction device 1000 generally consists of a cylinder and piston assembly 1001 to contain the reservoir sample within the cylinder. The piston mechanically compresses the sample within the cylinder. The cylinder defines a bottom opening 1001a. The bottom opening is covered by a basal assembly 1002 containing a filter means for retaining the solid portion of a sample, while allowing for efficient transfer of the fluid portions comprising gas, water and oil to flow through. In one embodiment, the filter means comprises a combination of filter elements such as a fine screen mesh, a porous medium disc or a frit. In one embodiment, the basal assembly 1002 is pressure sealed against the cylinder by a thermally stable O-ring assembly to provide a complete high pressure seal. The filter means obviously minimizes sand and clay migration through the bottom opening 1001a, but allow bitumen and heavy oil to flow into a sample vial or sealable pressure vessel 1005, which may be contained within a collection chamber (not shown). The device also includes a press 1003 and preferably includes a heating jacket 1004 associated with the cylinder. Preferably, the device is mounted in a frame 1006 for mechanical stability. The heating element and the press may be operatively connected to a controller 1010 which may be manually controlled or automatically controlled by computer program.

The cylinder and piston assembly 1001, the filter and the basal assembly 1002 must of course be robust enough to withstand the pressure necessary to mechanically extract samples through the filter. In one embodiment, the unit pressure required is above about 50 MPa, and more preferably greater than about 100 MPa. In one embodiment, for most samples, the necessary pressure may be about 120 MPa (9 tons per square inch of the cylinder cross-sectional area) and may exceed 160-200 MPa (12-15 tons per square inch). In one embodiment, the cylinder comprises a steel cylinder of 8 inches in length, having an inside diameter of 2 inches, and an outside diameter of at least about 2.5 inches, and preferably about 3 inches. Of course, the dimensions may vary depending on the intended sample size, the inherent strength of the material used, and the target pressure to be used.

The piston may be machined to close tolerance to the inside diameter of the cylinder, so as to prevent or minimize leakage between the piston and the cylinder. In a preferred embodiment, it is preferred that the piston have a relatively long skirt which increases piston to cylinder contact area for better sealing, and also improves the stability of the piston within the cylinder. In one preferred embodiment, one or more piston rings (not shown) provide(s) a more complete seal, and may comprise a polymer ring seal, which is inert to chemicals and stable at high temperatures, for example up to 200° C. A seal of this type allows complete retention and recovery of any gas and light end compounds present in the bitumen.

In one embodiment, the filter elements are disposed at the bottom of the cylinder by the basal assembly 1002 which fits closely with the bottom of the cylinder. In order to prevent or minimize leakage between the cylinder and the basal assembly 1002, it is preferable to have a circular recess within which the cylinder fits, which recess has a diameter which closely matches the outside diameter of the cylinder.

A number of implementations have been described. Nevertheless, it will be understood that various modifications may be made. For example, other methods described herein besides those, or in addition to those, illustrated in FIGS. 5A-5B can be performed. Further, the illustrated steps of methods 500 and/or 550 can be performed in different orders, either concurrently or serially. Further, steps can be performed in addition to those illustrated in methods 500 and/or 500, and some steps illustrated in methods 500 and/or 550 can be omitted without deviating from the present disclosure. Further, various combinations of the components described herein may be provided for implementations of similar apparatuses. Accordingly, other implementations are within the scope of the present disclosure.

The invention claimed is:

1. A system for sampling a subsurface reservoir comprising:
   a sampling device comprising a cylindrical member that comprises a closed distal end and an end member that extends from the closed distal end, the end member configured to extend a first distance beyond the closed distal end and penetrate into a wall of a borehole drilled in a subterranean reservoir to a first depth; and
   a sampling and recovery system positioned within the cylindrical member and configured to:
      penetrate through the closed distal end of the cylindrical member and into the subterranean reservoir to a second depth that is greater than the first depth; and
      recover a sample of reservoir material or reservoir fluids from the reservoir.

2. The system of claim 1, wherein the cylindrical member further comprises an inner lumen, and the sampling and recovery system comprises at least one of:
   a drill bit configured to penetrate through the closed distal end of the cylindrical member and into the subterranean reservoir to the second depth; or
   a cannula configured to penetrate through the closed distal end of the cylindrical member and into the subterranean reservoir to the second depth.

3. The system of claim 2, wherein the cannula comprises a side-port cannula.

4. The system of any of claims 1-3, wherein:
   the first depth is greater than a thickness of at least one of a contaminated layer coating the wall or invaded into the reservoir; and
   the sample is substantially free of contaminants from the contaminated layer.

5. The system of claim 1, wherein the sampling device is positionable on a tool configured to be lowered into a borehole formed in the reservoir.

6. The system of claim 1, wherein multiple sampling devices are positionable on the tool configured to be lowered into the borehole formed in the reservoir.

7. The system of claim 1, wherein the closed distal end of the cylindrical member is configured to open outwardly flower-style into the reservoir when drilled through by the drill bit.

8. The system of claim 1, wherein the closed distal end of the cylindrical member comprises an exit area which can be drilled through once the cylindrical member is drilled into the reservoir.

9. The system of claim 1, wherein the sample comprises heavy oil or bitumen or reservoir water, the system further comprising:
   an extraction device configured to extract heavy oil or bitumen from the sample; and
   an analysis device configured to receive the extracted heavy oil or bitumen and determine one or more properties of the extracted heavy oil or bitumen.

10. The system of claim 9, wherein the extraction device extracts the heavy oil or bitumen in situ in the borehole and the analysis device determines the one or more properties of the extracted heavy oil or bitumen in situ.

11. The system of claim 9, wherein the analysis device comprises a viscometer or rheometer configured to determine an absolute viscosity of the extracted heavy oil or bitumen solution.

12. A system for sampling a subsurface reservoir comprising:
   a sampling device comprising a cylindrical member that comprises a closed distal end and an end member that extends from the closed distal end, the end member configured to extend a first distance beyond the closed distal end and penetrate into a wall of a borehole drilled in a subterranean reservoir to a first depth;
   a sampling tube positioned within the cylindrical member;
   a penetration device positioned within the sampling tube and configured to penetrate through the closed distal end of the cylindrical member and into the subterranean reservoir to a second depth that is greater than the first depth;
   a solvent injecting device configured to extend from the sampling tube and inject a spectroscopically distinct polar solvent into the reservoir, wherein the solvent extracts a fluid sample from the reservoir; and a pump configured to withdraw fluid from the reservoir into the solvent injecting device, the fluid comprising the solvent and the fluid sample.

13. The system of claim 12, wherein the fluid sample comprises an oil sample, a water sample, or an oil and water sample.

14. The system of claim 12, wherein the penetration device comprises one of a drill bit or a cannula.

15. A method for sampling a subsurface reservoir performed with the system of claim 14, the method comprising:
in response to drilling the drill bit through the closed distal end of the cylindrical member, the distal end opens outwardly flower-style into the reservoir.

16. The method of claim 15, further comprising:
in response to drilling the drill bit through the closed distal end of the cylindrical member, the drill bit drills through a soft metal or polymer end component.

17. The method of claim 15, further comprising determining a property of the fluid sample.

18. The method of claim 17, wherein the property comprises at least one of:
a viscosity of a heavy oil or bitumen extracted from the fluid sample;
an oil saturation of the heavy oil or bitumen extracted from the fluid sample;
a water saturation in the reservoir;
an API of the heavy oil or bitumen extracted from the fluid sample;
a gas oil ratio (GOR) of the heavy oil or bitumen extracted from the fluid sample;
a formation volume factor or other PVT parameter of the heavy oil or bitumen extracted from the fluid sample;
a TAN of the heavy oil or bitumen extracted from the fluid sample;
a pourpoint of the heavy oil or bitumen extracted from the fluid sample; or
a Conradson carbon of the heavy oil or bitumen extracted from the fluid sample.

19. The method of claim 17, wherein determining the property comprises determining the property using multivariate analysis of one or more spectral responses.

20. The method of claim 19, wherein the one or more spectral responses comprise one or more responses based on mass or light-based spectroscopy, one or more responses from an electronic nose, or one or more responses from non-spectroscopic sensors.

21. The method of claim 17, wherein determining the property comprises determining the property in situ in the borehole.

22. The method of claim 17, wherein determining the property comprises determining the property at a terranean surface after removing the fluid sample from the borehole.

23. The method of claim 15, further comprising:
determining a concentration in the oils of crude oil components comprising alkanes or aromatic hydrocarbons using multivariate analysis of the spectral responses.

24. The method of claim 15, further comprising:
assessing at least one of a plurality of reservoir compartments or intra reservoir barriers using concentrations of at least one of saturated hydrocarbons, aromatic hydrocarbons, or thioaromatic compounds.

25. The method of claim 24, wherein the aromatic hydrocarbons or thioaromatic compounds comprise at least one of alkylbenzenes, alkylnaphthalenes, alkylbenzothiophenes, alkyldibenzothiophenes, or alkylphenanthrenes.

26. The method of claim 15, further comprising extracting an oil sample from the reservoir using a hydrophobic solvent.

27. The method of claim 15, further comprising extracting a water sample from the reservoir using a hydrophilic solvent.

28. The method of claim 15, further comprising extracting a combined oil and water sample from the reservoir using a mixture of a hydrophobic and a hydrophilic solvent.

29. The method of claim 15, further comprising extracting a combined oil and water sample from the reservoir using a mixture of dichloromethane and methanol.

30. The method of claim 15, further comprising at least one of:
extracting an oil sample from the reservoir using at least one of hexane, toluene, dichloromethane (DCM), chloroform, carbon tetrachloride, or carbon disulfide; or
extracting an oil sample from the reservoir using an isotopically-labeled hydrocarbon that has distinctive spectrometric properties different from those of crude oils.

31. The method of claim 15, further comprising extracting a water sample from the reservoir using at least one of a single alcohol, a mixture of alcohols, or a ketone that have distinctive spectrometric properties different from those of water.

32. The system of claim 12, further comprising an analysis device operatively connected to the solvent injecting and recovery device and configured to receive the withdrawn fluid and determine one or more properties of the fluid while in situ in the reservoir.

33. The system of claim 32, wherein the analysis device comprises:
a spectrometer or sensor configured to determine a concentration of oil or solvent in the fluid sample; and
a viscometer configured to determine a viscosity of the oil in the fluid sample.

34. The system of claim 32, wherein the analysis device comprises a viscometer configured to determine a viscosity of oil in the fluid sample.

35. The system of claim 32, wherein the analysis device comprises:
a spectrometer or sensor configured to determine the spectral properties of the reservoir fluid sample and a concentration of oil in the fluid sample.

36. The system of claim 32, wherein the analysis device comprises:
a spectrometer configured to determine the spectral properties of the reservoir fluid sample.

37. The system of claim 32, wherein the analysis device comprises a spectrometer configured to determine the spectral properties of the reservoir fluid sample and a concentration of water in the fluid sample.

38. The system of claim 12, wherein the solvent injecting device comprises a sampling bit configured to screw into the reservoir.

* * * * *